(12) United States Patent
Johnson et al.

(10) Patent No.: US 7,189,694 B2
(45) Date of Patent: Mar. 13, 2007

(54) INHIBITORS OF AUTOPHOSPHORYLATION PROTEIN KINASES

(75) Inventors: Howard M. Johnson, Gainesville, FL (US); Prem S. Subramaniam, Gainsville, FL (US); Mustafa G. Mujtaba, Gainesville, FL (US); Lawrence Flowers, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 113 days.

(21) Appl. No.: 10/828,151

(22) Filed: Apr. 19, 2004

(65) Prior Publication Data

US 2004/0265963 A1     Dec. 30, 2004

Related U.S. Application Data

(60) Provisional application No. 60/463,929, filed on Apr. 18, 2003.

(51) Int. Cl.
| | |
|---|---|
| *A61K 38/08* | (2006.01) |
| *A61K 38/10* | (2006.01) |
| *A61K 38/16* | (2006.01) |
| *C07K 7/06* | (2006.01) |
| *C07K 7/08* | (2006.01) |
| *C07K 14/00* | (2006.01) |

(52) U.S. Cl. .......................... 514/12; 514/13; 514/14; 514/15; 514/16; 514/17; 530/324; 530/326; 530/327; 530/328; 530/329

(58) Field of Classification Search .................... None
See application file for complete search history.

(56) References Cited

U.S. PATENT DOCUMENTS

| | | | | |
|---|---|---|---|---|
| 4,179,337 | A | 12/1979 | Davis et al. | ................. 435/181 |
| 5,034,322 | A | 7/1991 | Rogers et al. | ............ 435/172.3 |
| 5,106,739 | A | 4/1992 | Comai et al. | ............ 435/172.3 |
| 5,346,888 | A * | 9/1994 | Lipsky et al. | .................. 514/19 |
| 5,530,101 | A | 6/1996 | Queen et al. | ............ 530/387.3 |
| 5,585,089 | A | 12/1996 | Queen et al. | ............ 424/133.1 |
| 5,625,136 | A | 4/1997 | Koziel et al. | ................ 800/205 |
| 5,693,762 | A | 12/1997 | Queen et al. | ............ 530/387.3 |
| 5,763,585 | A | 6/1998 | Nag | ........................... 530/413 |
| 5,854,204 | A * | 12/1998 | Findeis et al. | .................. 514/2 |
| 5,912,183 | A | 6/1999 | Comoglio et al. | ........... 436/501 |
| 5,919,455 | A * | 7/1999 | Greenwald et al. | ....... 424/178.1 |
| 6,180,370 | B1 | 1/2001 | Queen et al. | ............... 435/69.6 |
| 6,407,213 | B1 | 6/2002 | Carter et al. | ............. 530/387.3 |
| 2001/0028879 | A1 * | 10/2001 | Spaner | ...................... 424/93.7 |
| 2002/0035243 | A1 | 3/2002 | Imfeld et al. | ................ 530/408 |
| 2002/0120100 | A1 | 8/2002 | Bonny | ......................... 530/322 |
| 2003/0032594 | A1 | 2/2003 | Bonny | ......................... 514/12 |
| 2003/0050455 | A1 * | 3/2003 | Ruben et al. | .............. 536/23.1 |

OTHER PUBLICATIONS

Alexander, W. "Suppressors of Cytokine Signaling (SOCS) in the Immune System" *Nature Review Immunology*, Jun. 2002, pp. 1-7, vol. 2.
Andersson, L. "Significance of Tyrosine Kinases in Cancer: Overview" *European Journal of Cancer*, 2002, vol. 38, Suppl. 5 S2.
Blalock, J. et al. "Binding of Peptides that are Specified by Complementary RNAs" *Biochem. J.*, 1986, pp. 679-683, vol. 234.
Blume-Jensen, P. et al. "Oncogenic Kinase Signalling" *Nature*, May 2001, pp. 355-365, vol. 411.
Capdeville, R. et al. "Glivec (STI571, Imatinib), a Rationally Developed Targeted Anticancer Drug" *Nature Reviews Drug Recovery*, Jul. 2002, pp. 493-502, vol. 1.
De Boer, H. et al. "The *Tac* Promoter: a Functional Hybrid Derived From the *trp* and *lac* Promoters" *Proc. Natl. Acad. Sci. USA*, Jan. 1983, pp. 21-25, vol. 80.
Familletti, P. et al. "A Convenient and Rapid Cytopathic Effect Inhibition Assay for Interferon" *Methods in Enzymology*, 1981, pp. 387-394, vol. 78.
Felgner, P. et al. "Lipofection: A Highly Efficient, Lipid-medicated DNA-transfection Procedure" *Proc. Natl. Acad. Sci. USA*, Nov. 1987, pp. 7413-7417, vol. 84.
Ferrara, N. et al. "The Biology of VEGF and its Receptors" *Nature Medicine*, Jun. 2003, pp. 669-676, vol. 9, No. 6.
Hanada, T. et al. "Negative Regulation of Cytokine Signaling by CIS/SOCS Family Proteins and Their Roles in Inflammatory Diseases" *Rev. Physiol Biochem Pharmacol*, 2003, pp. 72-86, vol. 149.
Kile, B. et al. "The SOCS Box: A Tale of Destruction and Degradation" *Trends Biochem. Sci.*, May 2002, pp. 235-241, vol. 27, No. 5.
Kotenko, S. et al. "Jak-Stat Signal Transduction Pathway Through the Eyes of Cytokine Class II Receptor Complexes" *Oncogene*, 2000, pp. 2557-2565, vol. 19.

(Continued)

*Primary Examiner*—Jeffrey Edwin Russel
(74) *Attorney, Agent, or Firm*—Saliwanchik, Lloyd & Saliwanchik

(57) ABSTRACT

The subject invention concerns peptide molecules that specifically inhibit the enzymatic function of tyrosine kinases, including the JAK and EGF receptor (EGFR) family of kinases, to autophosphorylate, i.e., to transfer a phosphate group from ATP to an amino acid in the kinase. Phosphorylation of proteins is the most fundamental method for signal transduction among proteins in a cell. Inhibition of tyrosine kinase autophosphorylation activities inhibits the enzyme's signaling and shuts down the functioning pathways originating from the enzyme. The JAK2 and EGFR tyrosine kinases are involved in both inflammatory disorders and cancer. In these disorders, the tyrosine kinases can often be activated in an uncontrolled fashion. The subject application also concerns antibodies that bind to a tyrosine kinase autophosphorylation site. The subject invention also concerns pharmaceutically acceptable formulations of the subject peptides and antibodies, and methods for treating inflammatory and oncological disorders by inhibiting tyrosine kinase signaling in these situations by administering a peptide or antibody of the present invention.

50 Claims, 8 Drawing Sheets

OTHER PUBLICATIONS

Kohler, G. et al. "Continuous Cultures of Fused Cells Secreting Antibody of Predefined Specificity" *Nature*, Aug. 1975, pp. 495-497, vol. 256.

Larsen, L. et al. "Suppressors of Cytokine Signalling: SOCS" *APMIS*, 2002, pp. 833-844, vol. 110.

Levitzki, A. "Tyrosine Kinases as Targets For Cancer Therapy" *European Journal of Cancer*, 2002, vol. 38, Suppl. 5, S11-S18.

Merrifield, R.B. "Solid Phase Peptide Synthesis. I. The Synthesis of a Tetrapeptide" *J. Amer. Chem. Soc.*, Jan. 31, 1963, pp. 2149-2154, vol. 85.

Ritter, C. et al. "The Epidermal Growth Factor Receptor-tyrosine Kinase: A Promising Therapeutic Target in Solid Tumors" *Semin. Oncol.*, Feb. 2003, pp. 3-11, vol. 30, No. 1, Suppl. 1.

Szente, B. et al. "Structural Requirements For Agonist Activity of a Murine Interferon-gamma Peptide" *J. Interferon Cytokine Res.*, 1996, pp. 813-817, vol. 16.

Tam, J. "Synthetic Peptide Vaccine Design: Synthesis and Properties of a High-density Multiple Antigenic Peptide System" *Proc. Natl. Acad. Sci. USA*, Aug. 1988, pp. 5409-5413, vol. 85.

Villain, M. et al. "*De Novo* Design of Peptides Targeted to the EF Hands of Calmodulin" *J. Biol. Chem.*, Jan. 28, 2000, pp. 2676-2685, vol. 275, No. 4.

Wells, A. "EGF Receptor" *Int. J. Biochem. Cell Biol.*, 1999, pp. 637-643, vol. 31, No. 6.

Xia, L. et al. "Identification of Both Positive and Negative Domains Within the Epidermal Growth Factor Receptor COOH-terminal Region for Signal Transducer and Activator of Transcription (STAT) Activation" *J. Biol. Chem.*, Aug. 23, 2002, pp. 30716-30723, vol. 277, No. 34.

Xu, D. et al. "Systemic Induction of a Potato *pin2* Promoter by Wounding, Methyl Jasmonate, and Abscisic Acid in Transgenic Rice Plants" *Plant Molecular Biology*, 1993, pp. 573-588, vol. 22.

Yasukawa, H. et al. "The JAK-binding Protein JAB Inhibits Janus Tyrosine Kinase Activity Through Binding in the Activation Loop" *EMBO J.*, 1999, pp. 1309-1320, vol. 18, No. 5.

Yu, Y. et al. "Direct Identification of a Major Autophosphorylation Site on Vascular Endothelial Growth Factor Receptor Flt-1 that Mediates Phosphatidylinositol 3'-kinase Binding" *Biochem J.*, 2001, pp. 465-472, vol. 358, Part A.

Faasina, G. et al. "Binding of Human Tumor Necrosis Factor α to Multimeric Complementary Peptides" *Archives of Biochemistry and Biophysics*, Jul. 1, 1992, pp. 137-143, vol. 296, No. 1.

Hobta, A. et al. "Epidermoid Carcinoma-Derived Antimicrobial Peptide (ECAP) Inhibits Phosphorylation by Protein Kinases *in vitro*" *Cell Biochemistry and Function*, 2001, pp. 291-298, vol. 19.

Kelloff, G. J. et al. "Epidermal Growth Factor Receptor Tyrosine Kinase Inhibitors as Potential Cancer Chemopreventives" *Cancer Epidemiology, Biomarkers and Prevention*, 1996, pp. 657-666, vol. 5.

Ohya K-I. et al. "SOCS-1/JAB/SSI-1 Can Bind to and Suppress Tec Protein-Tyrosine Kinase" *The Journal of Biological Chemistry*, 1997, pp. 27178-27182, vol. 272, No. 43.

\* cited by examiner

1. Jak2 alone
2. Jak2+IFNGR-1
3. Jak2+IFNGR-1+Tkip (50 μM)
4. Jak2+IFNGR-1+Control peptide (50 μM)
5. Jak2+IFNGR-1+Genistein (10 μM)

1. VEGFR alone
2. VEGFR + Tkip (50 μM)
3. VEGFR + Control peptide (50 μM)

1: EGFR alone
2: EGFR + Tkip (50 μM)
3: EGFR + Control peptide (50 μM)

1. Jak2 alone
2. Jak2+IFNGR-1
3. Jak2+IFNGR-1+Tkip (50 μM)
4. Jak2+IFNGR-1+Control peptide (50 μM)

1. Media
2. IFN alone
3. IFN + 95-125
4. IFN + Lipo-Tkip, 8 M
5. IFN + Lipo-Tkip, 1 M
6. Lipo-Tkip alone, 8 M 1. Media
2. VEGF alone
3. VEGF + 95-125
4. VEGF + Lipo-Tkip, 8 M
5. VEGF + Lipo-Tkip, 1 M
6. Lipo-Tkip alone, 8 M 1. Jak2 alone
2. Jak2 + IFNGR-1
3. Jak2 + IFNGR-1 + Tkip Peptide (50 μM)
4. Jak2 + IFNGR-1 + NGVLFLMIFHFLG (50 μM)
5. Jak2 + IFNGR-1 + Control Peptide (50 μM)
6. Jak2 + IFNGR-1 + Genistein (10 μM)
7. Jak2 + IFNGR-1 + EMLVLLMALKLLA Peptide (50 μM)

INHIBITORS OF AUTOPHOSPHORYLATION PROTEIN KINASES

CROSS REFERENCE TO RELATED APPLICATION

This application claims the benefit of U.S. Provisional Application Ser. No. 60/463,929, filed Apr. 18, 2003.

This invention was made with government support under National Institute of Health Grant Nos. AI025904 and AI56152. The Government has certain rights in the invention.

BACKGROUND OF THE INVENTION

Protein kinases represent a large number of structurally related enzymes that are involved in signal transduction processes within cells. The basic mechanism of action of protein kinases is to add a phosphate group (i.e., phosphorylation) to a protein. Protein kinases have been classified into various groups based on the substrates phosphorylated by the protein kinase. For example, tyrosine kinase phosphorylates protein at a tyrosine residue and serine kinase phosphorylates protein at a serine residue. A large number of cellular processes and functions are regulated by protein kinases. These include proliferation, differentiation, apoptosis, gene transcription, and protein translation.

Tyrosine kinases catalyze the transfer of a terminal phosphate of adenosine triphosphate (ATP) to a tyrosine residue in the protein substrate. A kinase that phosphorylates one or more of its own tyrosines is an autophosphorylation tyrosine kinase. Tyrosine kinases can be classified as those that autophosphorylate, or those that do not autophosphorylate but that do phosphorylate other proteins. Tyrosine kinases are also classified as receptor type or non-receptor type. The receptor-type tyrosine kinases have an extracellular region, a transmembrane region, and an intracellular region. Non-receptor type tyrosine kinases are located intracellularly. There are several subgroups of the receptor-type tyrosine kinases including the group designated as HER. The HER subgroup of tyrosine kinases includes EGF receptor, HER2, HER3, and HER4 (also known as erbB-1, erbB-2, erbB-3, and erbB-4, respectively). Tyrosine kinases play an important role in both normal and abnormal cell function (Blume-Jensen et al., 2001; Andersson 2002; Levitzki 2002; Alton et al., 2002). Uncontrolled or constitutive tyrosine kinase activity can result in diseases such as cancer and immunological disorders associated with inflammatory or T-helper 1 lymphocytes (Blume-Jensen et al., 2001; Tsygankov, A. Y. 2003; Andersson 2002; Levitzki 2002; Alton et al., 2002). Many oncogenes code for proteins that are tyrosine kinases (Blume-Jensen et al., 2001).

Some growth factors and cytokines regulate cellular functions by way of the Janus Kinase (JAK) signal transducers and activators of transcription (STAT). The JAK tyrosine kinases are typically activated upon ligand binding to a receptor-type tyrosine kinase. Transcription factors (STATS) are then activated by phosphorylation. It is thought that the activated STATS are then directed to the nucleus and are subsequently involved in transcription of a target gene. The JAK family of tyrosine kinases were first described for their role in signaling through the interferon (IFN) receptors of both type I and type II IFNs (Kotenko et al., 2000). Among the IFNs, JAK2 is associated with the type II IFN, IFN-γ (Kotenko et al., 2000). The immediate-early signal transduction events associated with IFNγ's interaction with its receptor involves the obligatory action of two tyrosine kinases, JAK1 and JAK2 (Kotenko et al., 2000). The IFN-γ receptor (IFNGR) system is a heterodimeric complex consisting of an α-subunit, IFNGR-1, and a β-subunit, IFNGR-2, both of which are essential for biological activities of IFN-γ (Kotenko et al., 2000). JAK1 is constitutively associated with the IFNGR-1 chain, while JAK2 is associated with the IFNGR-2 chain (Kotenko et al., 2000).

Interaction of IFN-γ, primarily with the IFNGR-1 subunit, initiates a sequence of events that results in increased binding of JAK2 to IFNGR-1 (Kotenko et al., 2000). This interaction has important consequences for subsequent critical phosphorylation events (Kotenko et al., 2000). JAK2, in the process of binding to IFNGR-1, undergoes autophosphorylation, and at the same time IFNGR-1 is phosphorylated. These events, occurring in concert with JAK1 function, result ultimately in recruitment and tyrosine phosphorylation of the IFN-γ transcription factor STAT1α (Kotenko et al., 2000). The activity of JAK tyrosine kinases, and consequently signaling via the JAK/STAT pathway, is controlled negatively by members of the suppressors of cytokine signaling family (SOCS), also called the cytokine-inducible SH2 containing (CIS) family (Hanada et al., 2003; Kile et al., 2002; Alexander 2002; Larsen et al., 2002). These inducible proteins are of significantly varied lengths, but share domains of homology that characterize the family and their function.

As noted above, many cancer genes code for proteins that are tyrosine kinases. Because of the association of tyrosine kinases with oncogenesis and cellular proliferation, inhibitors of tyrosine kinases are being actively developed and evaluated for their use in treating various oncological disorders. The targeted approach of treatment of cancer is directed towards development of specific tyrosine kinase inhibitors. One of the most successful examples of targeted therapy against cancer is in the treatment of chronic myelogenous leukemia (CML). This form of leukemia arises from chromosomal rearrangements where the p210 BCR-Abl cytoplasmic tyrosine kinase is rendered constitutively active. The pharmaceutical compound marketed under the name GLEEVEC (imatinib mesylate) (Novartis Pharmaceutical Company, East Hanover, N.J.) binds to the ATP binding site of this kinase and inhibits its kinase activity (Capdeville et al., 2002; Levitzki 2002). This results in almost total control of CML without the undesirable side effects typically associated with conventional chemotherapy.

U.S. Pat. No. 5,912,183 (Comoglio et al.) discloses peptides which interact with intracellular signal transducers, thereby interfering in pathways associated with cell proliferation, adhesion, etc. Peptides described in the '183 patent generally contain tyrosine residues and are modeled to represent sites of tyrosine phosphorylation. Another drug (Iressa; ZD1839) that inhibits the tyrosine kinase Epidermal Growth Factor Receptor is also in clinical trials for the treatment of cancer. U.S. Pat. No. 6,417,168, published U.S. application US 2002/0165193 and published reports by Park et al. describe peptidomimetics that bind to the $p185^{HER2/neu}$ growth factor receptor and inhibit proliferation of $p185^{HER2/neu}$ overexpressing tumor cells. The $p185^{HER2/neu}$ protein is the human analog of $p185^{neu}$. The $p185^{HER2/neu}$ protein is overexpressed in a significant percentage of cancers, including ovarian, breast, and colon cancer. The monoclonal antibody marketed under the name HERCEPTIN (trastuzumab) (Genentech, South San Francisco, Calif.) binds to the $p185^{HER2/neu}$ protein and is being used in clinical treatment of cancer (Ritter and Arteaga 2003).

However, most current therapeutics for cancer and inflammation are too nonspecific and thus not sufficiently effective. Further, chemotherapy, which is a highly non-specific treatment for cancer, is a non-targeted systemic approach to cancer treatment. As can be understood from the above, there remains a need in the art for drugs that are specifically targeted for cellular molecules that are involved or associated with inflammatory and/or oncological disorders. In particular, there remains a need for other inhibitors of tyrosine kinases, including those that are specifically inhibitory to certain kinds and classes of the tyrosine kinases.

BRIEF SUMMARY OF THE INVENTION

The subject invention concerns compounds and molecules, such as peptide molecules, that specifically inhibit the enzymatic function of tyrosine kinases, including the JAK and EGF receptor (EGFR) family of kinases, to autophosphorylate, i.e., to transfer a phosphate group from ATP to an amino acid in the kinase. Phosphorylation of proteins is the most fundamental method for signal transduction among proteins in a cell. Inhibition of tyrosine kinase autophosphorylation activities inhibits the enzyme's signaling and shuts down the functioning pathways originating from the enzyme. Specifically exemplified herein are peptides for inhibiting JAK2 and EFGR autophosphorylation. An antibody that binds to the autophosphorylation site of a kinase and blocks autophosphorylation is also included in the scope of the present invention. The JAK2 and EGFR tyrosine kinases are involved in both inflammatory disorders and cancer. In these disorders, the tyrosine kinases can often be activated in an uncontrolled fashion. Thus, the subject invention also concerns methods for treating inflammatory and oncological disorders by inhibiting tyrosine kinase signaling in these situations by administering a compound or molecule of the present invention.

BRIEF DESCRIPTION OF THE FIGURES

FIG. 1A shows direct binding of wild type JAK2 WT peptide (see Table 3 for sequences) to Tkip. The wild type JAK2 peptide was synthesized with a biotin group incorporated at its N-terminus during peptide synthesis, and the peptide purified. Biotinylated JAK2 WT peptide, at the indicated concentrations, was added in triplicate to wells of 96-well plates coated with either Tkip, VEGFR peptide, CDK-2 cyclin box peptide, or MuIFN-γ(95–125) peptide (see Table 3 for sequences). Wells were blocked with PBS+2% gelatin+0.1% Tween-20. The assay was developed using standard ELISA methods using a neutravidin-HRP conjugate to detect bound biotinylated wild type JAK2. Non-specific binding was determined from wells that were not coated with any peptide to which the same concentrations of biotinylated peptide were added. FIG. 1B shows biotinylated wild type JAK2 peptide was bound to Tkip coated on 96-well plates, either in the absence (100% binding) or presence of indicated concentrations of JAK2 WT peptide, VEGFR peptide or an unrelated peptide (MuIFN-γ(95–125)). Bound biotinylated wild type JAK2 peptide was detected by ELISA using a neutravidin-HRP conjugate. The data are representative of at least two separate experiments.

In FIG. 2A, Tkip inhibits autophosphorylation of JAK2. Tkip peptide was added at 50 µM, where indicated, to in vitro kinase assays measuring JAK2 autophosphorylation. Kinase reactions were subjected to SDS-PAGE and the gels dried. Dried gels were subjected to autoradiography to detect $^{32}$P-labeled proteins (upper and middle panels). The negative control peptide was the JAK2 WT peptide used at the same concentration. Genistein, a nonspecific inhibitor of JAK2, was used as a positive control. Total JAK2 protein was measured from separate reactions that were subjected to SDS-PAGE and the proteins Western transferred to a nitrocellulose membrane followed by detection with standard immunoblotting and ECL detection protocols (bottom panel). The data are representative of at least two separate experiments. In FIG. 2B, Tkip does not inhibit autophosphorylation of VEGFR. Tkip peptide was added at 50 µM, where indicated, to in vitro kinase assays measuring VEGFR autophosphorylation. The control peptide was the JAK2 WT peptide (see Table 3) used at the same concentration. Kinase reactions were subjected to SDS-PAGE and the gels dried. Dried gels were subjected to autoradiography to detect $^{32}$P-labeled proteins (upper panel). Total VEGFR protein was measured from separate reactions that were subjected to SDS-PAGE and the proteins Western transferred to a nitrocellulose membrane followed by detection with standard immunoblotting and ECL detection protocols (lower panel). In FIG. 2C, Tkip does not inhibit tyrosine phosphorylation activity of c-src. Tkip peptide was added at 50 µM, where indicated, to in vitro kinase assays measuring c-src tyrosine phosphorylation of a synthetic substrate peptide. C-src kinase activity was determined using a kit purchased from Upstate Biotechnology (Lake Placid, N.Y.). The control peptide (c-src+Control peptide) was the JAK2 WT peptide used at the same concentration. None represents reactions without c-src or peptides as a measure of background. Triplicate samples of the kinase reactions were spotted on P81 cellulose discs, and processed as described by the manufacturer. The discs were counted for radioactivity, and kinase activity is reported as percentage of the activity of the reaction containing neither Tkip nor control peptide (c-src alone), after subtraction of background (None). In FIG. 2D, Tkip inhibition of kinase reactions for JAK2 were setup as described in FIG. 2A as a positive control, but samples were processed as in FIG. 2C. Activity is reported as percentage of activity in reactions containing JAK2 and IFNGR-1 alone, after subtraction of background. In FIG. 2E, Tkip peptide inhibits autophosphorylation of EGFR. Tkip peptide was added at 50 µM, where indicated, to in vitro kinase assays measuring EGFR autophosphorylation. The negative control peptide, 50 µM, was the same as in FIG. 2A (JAK2 WT, see Table 3). Kinase reactions were subjected to SDS-PAGE and the gels dried. Dried gels were subjected to autoradiography to detect $^{32}$P-labeled proteins (upper panel). Total EGFR protein was measured from separate reactions that were subjected to SDS-PAGE and the proteins Western transferred to a nitrocellulose membrane followed by detection with standard immunoblotting and ECL detection protocols (lower panel). In FIG. 2F, as a positive control, we demonstrate that Tkip inhibited JAK2 in the same experiment. Samples were set up and run as in FIG. 2A. This experiment was run in parallel with that of FIGS. 2B and 2E.

In FIG. 3A, Tkip was incubated with JAK2, IFNGR-1, and $^{32}$P-ATP for 30 min at 30° C. at the indicated concentrations. The kinase reaction was resolved on a 10% SDS-PAGE. The gel was dried and exposed to photographic film for 1 hr at −70° C. to detect phosphorylated proteins (upper panel). Kinase reaction mixtures were subjected to immunoblotting with a probe specific for JAK2 and IFNGR-1 as an internal protein loading control (second and fourth panel). In FIG. 3B, Tkip was incubated with EGF, EGFR, and $^{32}$P-ATP for 10 min at 30° C. at the indicated concentrations. The kinase reaction was resolved on a 10% SDS-PAGE. The gel was dried and exposed to photographic film for 1 hr at −70° C. to detect phosphorylated proteins (upper panel). Kinase reaction mixtures were subjected to immunoblotting with a probe specific for EGFR as an internal protein loading control (lower panel). The data are representative of at least two separate experiments.

In FIG. 5A, serum-starved WISH cells were pretreated with media alone or Tkip (8 μM or 1 μM) for 17 hr. Following 30 min incubation in the presence or absence of 5000 U/ml IFN-γ, cells were washed, harvested, and lysed. Whole cell extracts were resolved by 12% SDS-PAGE, transferred to nitrocellulose membranes, and examined using specific antibodies to phosphorylated STAT1α (p-Tyr 701, upper panel). The membrane was striped and reprobed with antibodies specific to unphosphorylated STAT1α to demonstrate equal protein loading (lower panel). Data are representative of at least two separate experiments. In FIG. 5B, BAECs were pretreated with media alone or Tkip (8 μM or 1 μM) overnight prior to 2 hr incubation in serum free media. Following starvation, BAECs were treated with or without 50 ng/ml of VEGF for 15 min in the presence or absence of various concentrations of Tkip (8 μM or 1 μM). VEGFR phosphorylation was monitored using immunoprecipation (anti-VEGFR) and immunoblot (anti-pY) analysis. The membrane was striped and reprobed with antibodies specific to VEGFR to demonstrate equal protein loading (lower panel). Data are representative of at least two separate experiments.

In FIG. 7A, WISH cells were treated in the presence or absence of IFN-γ (5000 U/ml) and various concentrations of Lipo-Tkip (LT) for 48 h. Cells were then stained with R-PE conjugated monoclonal antibody specific for human MHC class I. R-PE conjugated mouse IgG2a was used as an isotype control. The data are presented as mean fluorescence intensity. In FIG. 7B, overlapping histograms indicate untreated cells (bold line), IFN-γ treated cells (dashed line), and LT+IFN-γ treated cells (thin line).

BRIEF DESCRIPTION OF THE SEQUENCES

Figure 1A:
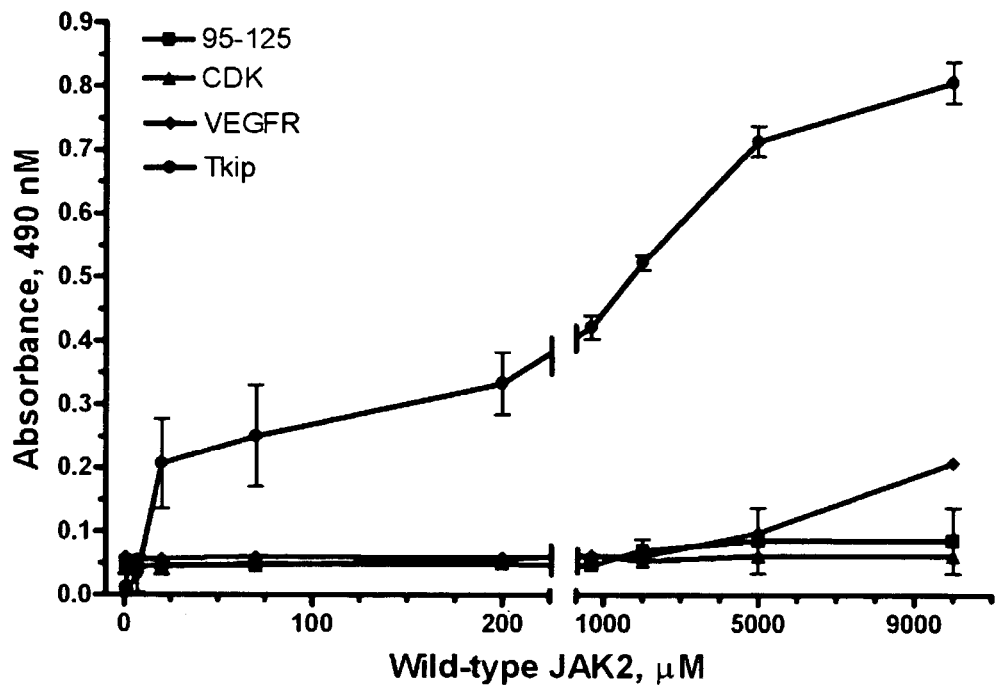
FIGS. 1A and 1B show the binding of Tkip peptide by JAK2 autophosphorylation peptide, JAK2 WT.

SEQ ID NO. 1 is the amino acid sequence of a peptide that can be used according to the present invention.

SEQ ID NO. 2 is the amino acid sequence of a peptide used for control purposes.

SEQ ID NO. 3 is an amino terminal deletion of the amino acid sequence shown in SEQ ID NO. 1.

SEQ ID NO. 4 is an amino terminal deletion of the amino acid sequence shown in SEQ ID NO. 1.

SEQ ID NO. 5 is an amino terminal deletion of the amino acid sequence shown in SEQ ID NO. 1.

SEQ ID NO. 6 is an amino terminal deletion of the amino acid sequence shown in SEQ ID NO. 1.

SEQ ID NO. 7 is an amino terminal deletion of the amino acid sequence shown in SEQ ID NO. 1.

SEQ ID NO. 8 is a carboxy terminal deletion of the amino acid sequence shown in SEQ ID NO. 1.

SEQ ID NO. 9 is a carboxy terminal deletion of the amino acid sequence shown in SEQ ID NO. 1.

SEQ ID NO. 10 is a carboxy terminal deletion of the amino acid sequence shown in SEQ ID NO. 1.

SEQ ID NO. 11 is a carboxy terminal deletion of the amino acid sequence shown in SEQ ID NO. 1.

SEQ ID NO. 12 is a carboxy terminal deletion of the amino acid sequence shown in SEQ ID NO. 1.

SEQ ID NO. 13 is an amino and carboxy terminal deletion of the amino acid sequence shown in SEQ ID NO. 1.

SEQ ID NO. 14 is an amino and carboxy terminal deletion of the amino acid sequence shown in SEQ ID NO. 1.

SEQ ID NO. 15 is an amino and carboxy terminal deletion of the amino acid sequence shown in SEQ ID NO. 1.

SEQ ID NO. 16 is an amino terminal addition of the amino acid sequence shown in SEQ ID NO. 1.

SEQ ID NO. 17 is an amino terminal addition of the amino acid sequence shown in SEQ ID NO. 1.

SEQ ID NO. 18 is an amino terminal addition of the amino acid sequence shown in SEQ ID NO. 1.

SEQ ID NO. 19 is an amino terminal addition of the amino acid sequence shown in SEQ ID NO. 1.

SEQ ID NO. 20 is an amino terminal addition of the amino acid sequence shown in SEQ ID NO. 1.

SEQ ID NO. 21 is an amino terminal addition of the amino acid sequence shown in SEQ ID NO. 1.

SEQ ID NO. 22 is an amino terminal addition of the amino acid sequence shown in SEQ ID NO. 1.

SEQ ID NO. 23 is a carboxy terminal addition of the amino acid sequence shown in SEQ ID NO. 1.

SEQ ID NO. 24 is a carboxy terminal addition of the amino acid sequence shown in SEQ ID NO. 1.

SEQ ID NO. 25 is a carboxy terminal addition of the amino acid sequence shown in SEQ ID NO. 1.

SEQ ID NO. 26 is a carboxy terminal addition of the amino acid sequence shown in SEQ ID NO. 1.

SEQ ID NO. 27 is a carboxy terminal addition of the amino acid sequence shown in SEQ ID NO. 1.

SEQ ID NO. 28 is a carboxy terminal addition of the amino acid sequence shown in SEQ ID NO. 1.

SEQ ID NO. 29 is a carboxy terminal addition of the amino acid sequence shown in SEQ ID NO. 1.

SEQ ID NO. 30 is an amino and carboxy terminal addition of the amino acid sequence shown in SEQ ID NO. 1.

SEQ ID NO. 31 is an amino and carboxy terminal addition of the amino acid sequence shown in SEQ ID NO. 1.

SEQ ID NO. 32 is an amino and carboxy terminal addition of the amino acid sequence shown in SEQ ID NO. 1.

SEQ ID NO. 33 is an amino and carboxy terminal addition of the amino acid sequence shown in SEQ ID NO. 1.

SEQ ID NO. 34 is an amino and carboxy terminal addition of the amino acid sequence shown in SEQ ID NO. 1.

SEQ ID NO. 35 is an amino and carboxy terminal addition of the amino acid sequence shown in SEQ ID NO. 1.

SEQ ID NO. 36 is an amino and carboxy terminal addition of the amino acid sequence shown in SEQ ID NO. 1.

SEQ ID NO. 37 is the amino acid sequence of a peptide that can be used according to the present invention.

SEQ ID NO. 38 is an amino terminal deletion of the amino acid sequence shown in SEQ ID NO. 37.

SEQ ID NO. 39 is an amino terminal deletion of the amino acid sequence shown in SEQ ID NO. 37.

SEQ ID NO. 40 is an amino terminal deletion of the amino acid sequence shown in SEQ ID NO. 37.

SEQ ID NO. 41 is an amino terminal deletion of the amino acid sequence shown in SEQ ID NO. 37.

SEQ ID NO. 42 is an amino terminal deletion of the amino acid sequence shown in SEQ ID NO. 37.

SEQ ID NO. 43 is a carboxy terminal deletion of the amino acid sequence shown in SEQ ID NO. 37.

SEQ ID NO. 44 is a carboxy terminal deletion of the amino acid sequence shown in SEQ ID NO. 37.

SEQ ID NO. 45 is a carboxy terminal deletion of the amino acid sequence shown in SEQ ID NO. 37.

SEQ ID NO. 46 is a carboxy terminal deletion of the amino acid sequence shown in SEQ ID NO. 37.

SEQ ID NO. 47 is a carboxy terminal deletion of the amino acid sequence shown in SEQ ID NO. 37.

SEQ ID NO. 48 is an amino and carboxy terminal deletion of the amino acid sequence shown in SEQ ID NO. 37.

SEQ ID NO. 49 is an amino and carboxy terminal deletion of the amino acid sequence shown in SEQ ID NO. 37.

SEQ ID NO. 50 is an amino and carboxy terminal deletion of the amino acid sequence shown in SEQ ID NO. 37.

SEQ ID NO. 51 is an amino terminal addition of the amino acid sequence shown in SEQ ID NO. 37.

SEQ ID NO. 52 is an amino terminal addition of the amino acid sequence shown in SEQ ID NO. 37.

SEQ ID NO. 53 is an amino terminal addition of the amino acid sequence shown in SEQ ID NO. 37.

SEQ ID NO. 54 is an amino terminal addition of the amino acid sequence shown in SEQ ID NO. 37.

SEQ ID NO. 55 is an amino terminal addition of the amino acid sequence shown in SEQ ID NO. 37.

SEQ ID NO. 56 is an amino terminal addition of the amino acid sequence shown in SEQ ID NO. 37.

SEQ ID NO. 57 is an amino terminal addition of the amino acid sequence shown in SEQ ID NO. 37.

SEQ ID NO. 58 is a carboxy terminal addition of the amino acid sequence shown in SEQ ID NO. 37.

SEQ ID NO. 59 is a carboxy terminal addition of the amino acid sequence shown in SEQ ID NO. 37.

SEQ ID NO. 60 is a carboxy terminal addition of the amino acid sequence shown in SEQ ID NO. 37.

SEQ ID NO. 61 is a carboxy terminal addition of the amino acid sequence shown in SEQ ID NO. 37.

SEQ ID NO. 62 is a carboxy terminal addition of the amino acid sequence shown in SEQ ID NO. 37.

SEQ ID NO. 63 is a carboxy terminal addition of the amino acid sequence shown in SEQ ID NO. 37.

SEQ ID NO. 64 is a carboxy terminal addition of the amino acid sequence shown in SEQ ID NO. 37.

SEQ ID NO. 65 is an amino and carboxy terminal addition of the amino acid sequence shown in SEQ ID NO. 37.

SEQ ID NO. 66 is an amino and carboxy terminal addition of the amino acid sequence shown in SEQ ID NO. 37.

SEQ ID NO. 67 is an amino and carboxy terminal addition of the amino acid sequence shown in SEQ ID NO. 37.

SEQ ID NO. 68 is an amino and carboxy terminal addition of the amino acid sequence shown in SEQ ID NO. 37.

SEQ ID NO. 69 is an amino and carboxy terminal addition of the amino acid sequence shown in SEQ ID NO. 37.

SEQ ID NO. 70 is an amino and carboxy terminal addition of the amino acid sequence shown in SEQ ID NO. 37.

SEQ ID NO. 71 is an amino and carboxy terminal addition of the amino acid sequence shown in SEQ ID NO. 37.

SEQ ID NO. 72 is the amino acid sequence of a peptide that can be used according to the present invention.

SEQ ID NO. 73 is the amino acid sequence of a peptide used for control purposes.

SEQ ID NO. 74 is the amino acid sequence of a peptide used for control purposes.

SEQ ID NO. 75 is the amino acid sequence of a peptide used for control purposes.

SEQ ID NO. 76 is the amino acid sequence of a peptide used for control purposes.

SEQ ID NO. 77 is an amino terminal deletion of the amino acid sequence shown in SEQ ID NO. 72.

SEQ ID NO. 78 is an amino terminal deletion of the amino acid sequence shown in SEQ ID NO. 72.

SEQ ID NO. 79 is an amino terminal deletion of the amino acid sequence shown in SEQ ID NO. 72.

SEQ ID NO. 80 is an amino terminal deletion of the amino acid sequence shown in SEQ ID NO. 72.

SEQ ID NO. 81 is a carboxy terminal deletion of the amino acid sequence shown in SEQ ID NO. 72.

SEQ ID NO. 82 is a carboxy terminal deletion of the amino acid sequence shown in SEQ ID NO. 72.

SEQ ID NO. 83 is a carboxy terminal deletion of the amino acid sequence shown in SEQ ID NO. 72.

SEQ ID NO. 84 is a carboxy terminal deletion of the amino acid sequence shown in SEQ ID NO. 72.

SEQ ID NO. 85 is a carboxy terminal deletion of the amino acid sequence shown in SEQ ID NO. 72.

SEQ ID NO. 86 is an amino and carboxy terminal deletion of the amino acid sequence shown in SEQ ID NO. 72.

SEQ ID NO. 87 is an amino and carboxy terminal deletion of the amino acid sequence shown in SEQ ID NO. 72.

SEQ ID NO. 88 is an amino and carboxy terminal deletion of the amino acid sequence shown in SEQ ID NO. 72.

SEQ ID NO. 89 is an amino and carboxy terminal deletion of the amino acid sequence shown in SEQ ID NO. 72.

SEQ ID NO. 90 is an amino terminal addition of the amino acid sequence shown in SEQ ID NO. 72.

SEQ ID NO. 91 is an amino terminal addition of the amino acid sequence shown in SEQ ID NO. 72.

SEQ ID NO. 92 is an amino terminal addition of the amino acid sequence shown in SEQ ID NO. 72.

SEQ ID NO. 93 is an amino terminal addition of the amino acid sequence shown in SEQ ID NO. 72.

SEQ ID NO. 94 is an amino terminal addition of the amino acid sequence shown in SEQ ID NO. 72.

SEQ ID NO. 95 is an amino terminal addition of the amino acid sequence shown in SEQ ID NO. 72.

SEQ ID NO. 96 is an amino terminal addition of the amino acid sequence shown in SEQ ID NO. 72.

SEQ ID NO. 97 is an amino terminal addition of the amino acid sequence shown in SEQ ID NO. 72.

SEQ ID NO. 98 is an amino terminal addition of the amino acid sequence shown in SEQ ID NO. 72.

SEQ ID NO. 99 is an amino terminal addition of the amino acid sequence shown in SEQ ID NO. 72.

SEQ ID NO. 100 is an amino terminal addition of the amino acid sequence shown in SEQ ID NO. 72.

SEQ ID NO. 101 is an amino terminal addition of the amino acid sequence shown in SEQ ID NO. 72.

SEQ ID NO. 102 is an amino terminal addition of the amino acid sequence shown in SEQ ID NO. 72.

SEQ ID NO. 103 is an amino terminal addition of the amino acid sequence shown in SEQ ID NO. 72.

SEQ ID NO. 104 is an amino terminal addition of the amino acid sequence shown in SEQ ID NO. 72.

SEQ ID NO. 105 is a carboxy terminal addition of the amino acid sequence shown in SEQ ID NO. 72.

SEQ ID NO. 106 is a carboxy terminal addition of the amino acid sequence shown in SEQ ID NO. 72.

SEQ ID NO. 107 is a carboxy terminal addition of the amino acid sequence shown in SEQ ID NO. 72.

SEQ ID NO. 108 is a carboxy terminal addition of the amino acid sequence shown in SEQ ID NO. 72.

SEQ ID NO. 109 is a carboxy terminal addition of the amino acid sequence shown in SEQ ID NO. 72.

SEQ ID NO. 110 is a carboxy terminal addition of the amino acid sequence shown in SEQ ID NO. 72.

SEQ ID NO. 111 is a carboxy terminal addition of the amino acid sequence shown in SEQ ID NO. 72.

SEQ ID NO. 112 is a carboxy terminal addition of the amino acid sequence shown in SEQ ID NO. 72.

SEQ ID NO. 113 is a carboxy terminal addition of the amino acid sequence shown in SEQ ID NO. 72.

SEQ ID NO. 114 is a carboxy terminal addition of the amino acid sequence shown in SEQ ID NO. 72.

SEQ ID NO. 115 is a carboxy terminal addition of the amino acid sequence shown in SEQ ID NO. 72.

SEQ ID NO. 116 is a carboxy terminal addition of the amino acid sequence shown in SEQ ID NO. 72.

SEQ ID NO. 117 is a carboxy terminal addition of the amino acid sequence shown in SEQ ID NO. 72.

SEQ ID NO. 118 is a carboxy terminal addition of the amino acid sequence shown in SEQ ID NO. 72.

SEQ ID NO. 119 is a carboxy terminal addition of the amino acid sequence shown in SEQ ID NO. 72.

SEQ ID NO. 120 is an amino and carboxy terminal addition of the amino acid sequence shown in SEQ ID NO. 72.

SEQ ID NO. 121 is an amino and carboxy terminal addition of the amino acid sequence shown in SEQ ID NO. 72.

SEQ ID NO. 122 is an amino and carboxy terminal addition of the amino acid sequence shown in SEQ ID NO. 72.

SEQ ID NO. 123 is an amino and carboxy terminal addition of the amino acid sequence shown in SEQ ID NO. 72.

SEQ ID NO. 124 is an amino and carboxy terminal addition of the amino acid sequence shown in SEQ ID NO. 72.

SEQ ID NO. 125 is an amino and carboxy terminal addition of the amino acid sequence shown in SEQ ID NO. 72.

SEQ ID NO. 126 is an amino and carboxy terminal addition of the amino acid sequence shown in SEQ ID NO. 72.

SEQ ID NO. 127 is an amino and carboxy terminal addition of the amino acid sequence shown in SEQ ID NO. 72.

SEQ ID NO. 128 is an amino and carboxy terminal addition of the amino acid sequence shown in SEQ ID NO. 72.

SEQ ID NO. 129 is an amino and carboxy terminal addition of the amino acid sequence shown in SEQ ID NO. 72.

SEQ ID NO. 130 is an amino and carboxy terminal addition of the amino acid sequence shown in SEQ ID NO. 72.

SEQ ID NO. 131 is an amino and carboxy terminal addition of the amino acid sequence shown in SEQ ID NO. 72.

SEQ ID NO. 132 is an amino and carboxy terminal addition of the amino acid sequence shown in SEQ ID NO. 72.

SEQ ID NO. 133 is an amino and carboxy terminal addition of the amino acid sequence shown in SEQ ID NO. 72.

SEQ ID NO. 134 is an amino and carboxy terminal addition of the amino acid sequence shown in SEQ ID NO. 72.

DETAILED DISCLOSURE OF THE INVENTION

The subject invention pertains to compounds and molecules that can bind to the autophosphorylation site of a protein kinase and block or inhibit autophosphorylation of an amino acid within the site, thereby blocking functional activity of the protein kinase. An embodiment of the subject invention concerns peptides that block the ability of a tyrosine kinase, such as a Janus Kinase (JAK), to autophosphorylate. In one embodiment, a peptide of the invention inhibits the ability of a JAK2 tyrosine kinase to autophosphorylate. JAK2 is an essential kinase for phosphorylation events essential to the biological activity of the cytokine gamma interferon (IFNγ). Production of IFNγ, an antiviral cytokine, is associated with inflammatory disorders. Failure of JAK2 to autophosphorylate results in loss of IFNγ activity. JAK2 activation is also associated with other inflammatory cytokines such as interleukin-13. In addition, oncogenes involved in cancer, such as BCR-Abl, utilize JAK2 for phosphorylation of protooncogene products such as C-myc.

In an exemplified embodiment, a peptide of the invention comprises the amino acid sequence: $NH_2$-tryptophan(W)-leucine(L)-valine(V)-phenylalanine(F)-phenylalanine(F)-valine(V)-isoleucine(I)-phenylalanine(F)-tyrosine (Y)-phenylalanine(F)-phenylalanine(F)-arginine(R)-COOH, represented by the standard single letter symbols: WLVFFVIFYFFR (SEQ ID NO. 1), also referred to herein as "Tkip" for (Tyrosine Kinase Inhibitor Peptide), or a fragment or variant of the peptide that can bind to an autophosphorylation site of a protein kinase, such as JAK2, and inhibit autophosphorylation of the protein kinase.

In another embodiment, a peptide of the invention comprises the amino acid sequence: $NH_2$-asparagine(N)-glycine (G)-valine(V)-leucine(L)-phenylalanine(F)-leucine(L)-methionine(M)-isoleucine(I)-phenylalanine(F)-histidine (H)-phenylalanine(F)-leucine(L)-glycine(G)—COOH, represented by the standard single letter symbols: NGVLFLMIFHFLG (SEQ ID NO. 37), or a fragment or variant of the peptide that can bind to an autophosphorylation site of a protein kinase, such as JAK2, and inhibit autophosphorylation of the protein kinase.

In another embodiment, a peptide of the invention comprises the amino acid sequence: $NH_2$-glutamicacid(E)-methionine(M)-leucine(L)-valine(V)-leucine(L)-leucine(L)-methionine(M)-alanine(A)-leucine(L)-lysine(K)-leucine (L)-alanine(A)—COOH, represented by the standard single letter symbols: EMLVLLMALKLLA (SEQ ID NO. 72), or a fragment or variant of the peptide that can bind to an autophosphorylation site of a protein kinase, such as JAK2, and inhibit autophosphorylation of the protein kinase.

Peptides of the invention can be readily prepared using standard techniques known in the art, including chemical synthesis (Merrifield, 1963) and genetic engineering. The peptide WLVFFVIFYFFR (SEQ ID NO. 1) exemplified herein was designed to bind to the autophosphorylation site corresponding to the amino acids 1001 to 1013, $^{1001}$LPQDKEYYKVKEP$^{1013}$ (SEQ ID NO. 2), of human JAK2. Autophosphorylation of a tyrosine kinase is inhibited when an inhibitor peptide of the invention is bound to the autophosphorylation site of the tyrosine kinase, thereby blocking autophosphorylation at the site and, therefore, the biological functions normally associated or mediated by the activated tyrosine kinase are subsequently inhibited when the tyrosine kinase is unable to autophosphorylate.

JAK tyrosine kinases that are contemplated to be inhibited by a peptide of the invention include JAK1, JAK2, JAK3, JAK4, JAK5, JAK6, and JAK7. Peptides of the present invention can also inhibit autophosphorylation of EGF receptor (EGFR) tyrosine kinases, whose members (for example, HER2) are involved in several types of cancers. EGFR kinases, like JAK tyrosine kinases, are autophosphorylation kinases. The EGF family of receptor tyrosine kinases include EGFR (erbB-1), erbB-2, erbB-3, and erbB-4, all of which are contemplated within the scope of the present invention. Preferably, the kinases are human kinases or kinases of other mammals, such as dog, cat, horse, etc. Additional tyrosine kinases contemplated within the scope of those that can be inhibited by a peptide of the present invention include those that share amino acid sequence homology with the amino acid sequence of human JAK2 or EFGR protein at the site of autophosphorylation on the kinase.

Peptides of the subject invention include the specific peptides exemplified herein as well as equivalent peptides which may be, for example, somewhat longer or shorter than the peptides exemplified herein. For example, using the teachings provided herein, a person skilled in the art could readily make peptides having from 1 to about 15 or more amino acids added to one or both ends of a peptide of the subject invention. Examples of peptides having amino acids added to one or both ends of the exemplified peptides (SEQ ID NO. 1 and SEQ ID NO. 37) and contemplated within the scope of the present invention are shown in SEQ ID NO. 16 to SEQ ID NO. 36 and SEQ ID NO. 51 to SEQ ID NO. 71. Similarly, a person skilled in the art could readily prepare peptides in which 1 to about 5 amino acids are removed from one or both ends of a peptide of the subject invention. Examples of peptide fragments of the exemplified peptides and contemplated within the scope of the present invention are shown in SEQ ID NO. 3 to SEQ ID NO. 15 and SEQ ID NO. 39 to SEQ ID NO. 50. The subject invention includes, but is not limited to, the exemplified longer and shorter peptides. Peptides wherein 1 to about 15 amino acids are added to one or both ends of the peptide EMLVLLMALKLLA (SEQ ID NO. 72) or wherein 1 to about 5 amino acids are removed from one or both ends of the peptide are specifically exemplified below (wherein "X" in the sequence represents any amino acid):

```
MLVLLMALKLLA        (SEQ ID NO. 77)

LVLLMALKLLA         (SEQ ID NO. 78)

VLLMALKLLA          (SEQ ID NO. 79)
```

-continued

| | |
|---|---|
| LMALKLLA | (SEQ ID NO. 80) |
| EMLVLLMALKLL | (SEQ ID NO. 81) |
| EMLVLLMALKL | (SEQ ID NO. 82) |
| EMLVLLMALK | (SEQ ID NO. 83) |
| EMLVLLMAL | (SEQ ID NO. 84) |
| EMLVLLMA | (SEQ ID NO. 85) |
| MLVLLMALKLL | (SEQ ID NO. 86) |
| LVLLMALKL | (SEQ ID NO. 87) |
| VLLMALK | (SEQ ID NO. 88) |
| LLMAL | (SEQ ID NO. 89) |
| XEMLVLLMALKLLA | (SEQ ID NO. 90) |
| XXEMLVLLMALKLLA | (SEQ ID NO. 91) |
| XXXEMLVLLMALKLLA | (SEQ ID NO. 92) |
| XXXXEMLVLLMALKLLA | (SEQ ID NO. 93) |
| XXXXXEMLVLLMALKLLA | (SEQ ID NO. 94) |
| XXXXXXEMLVLLMALKLLA | (SEQ ID NO. 95) |
| XXXXXXXEMLVLLMALKLLA | (SEQ ID NO. 96) |
| XXXXXXXXEMLVLLMALKLLA | (SEQ ID NO. 97) |
| XXXXXXXXXEMLVLLMALKLLA | (SEQ ID NO. 98) |
| XXXXXXXXXXEMLVLLMALKLLA | (SEQ ID NO. 99) |
| XXXXXXXXXXXEMLVLLMALKLLA | (SEQ ID NO. 100) |
| XXXXXXXXXXXXEMLVLLMALKLLA | (SEQ ID NO. 101) |
| XXXXXXXXXXXXXEMLVLLMALKLLA | (SEQ ID NO. 102) |
| XXXXXXXXXXXXXXEMLVLLMALKLLA | (SEQ ID NO. 103) |
| XXXXXXXXXXXXXXXEMLVLLMALKLLA | (SEQ ID NO. 104) |
| EMLVLLMALKLLAX | (SEQ ID NO. 105) |
| EMLVLLMALKLLAXX | (SEQ ID NO. 106) |
| EMLVLLMALKLLAXXX | (SEQ ID NO. 107) |
| EMLVLLMALKLLAXXXX | (SEQ ID NO. 108) |
| EMLVLLMALKLLAXXXXX | (SEQ ID NO. 109) |
| EMLVLLMALKLLAXXXXXX | (SEQ ID NO. 110) |
| EMLVLLMALKLLAXXXXXXX | (SEQ ID NO. 111) |
| EMLVLLMALKLLAXXXXXXXX | (SEQ ID NO. 112) |
| EMLVLLMALKLLAXXXXXXXXX | (SEQ ID NO. 113) |
| EMLVLLMALKLLAXXXXXXXXXX | (SEQ ID NO. 114) |
| EMLVLLMALKLLAXXXXXXXXXXX | (SEQ ID NO. 115) |
| EMLVLLMALKLLAXXXXXXXXXXXX | (SEQ ID NO. 116) |
| EMLVLLMALKLLAXXXXXXXXXXXXX | (SEQ ID NO. 117) |
| EMLVLLMALKLLAXXXXXXXXXXXXXX | (SEQ ID NO. 118) |
| EMLVLLMALKLLAXXXXXXXXXXXXXXX | (SEQ ID NO. 119) |

-continued

```
XEMLVLLMALKLLAX                         (SEQ ID NO. 120)

XXEMLVLLMALKLLAXX                       (SEQ ID NO. 121)

XXXEMLVLLMALKLLAXXX                     (SEQ ID NO. 122)

XXXXEMLVLLMALKLLAXXXX                   (SEQ ID NO. 123)

XXXXXEMLVLLMALKLLAXXXXX                 (SEQ ID NO. 124)

XXXXXXEMLVLLMALKLLAXXXXXX               (SEQ ID NO. 125)

XXXXXXXEMLVLLMALKLLAXXXXXXX             (SEQ ID NO. 126)

XXXXXXXXEMLVLLMALKLLAXXXXXXXX           (SEQ ID NO. 127)

XXXXXXXXXEMLVLLMALKLLAXXXXXXXXX         (SEQ ID NO. 128)

XXXXXXXXXXEMLVLLMALKLLAXXXXXXXXXX       (SEQ ID NO. 129)

XXXXXXXXXXXEMLVLLMALKLLAXXXXXXXXXXX     (SEQ ID NO. 130)

XXXXXXXXXXXXEMLVLLMALKLLAXXXXXXXXXXXX   (SEQ ID NO. 131)

XXXXXXXXXXXXXEMLVLLMALKLLAXXXXXXXXXXXXX (SEQ ID NO. 132)

XXXXXXXXXXXXXXEMLVLLMALKLLAXXXXXXXXXXXXXX   (SEQ ID NO. 133)

XXXXXXXXXXXXXXXEMLVLLMALKLLAXXXXXXXXXXXXXXX (SEQ ID NO. 134)
```

Peptides included within the scope of the invention include peptides from about 5 to about 45 amino acids. Thus, within the scope of the invention are peptides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, and 45 amino acids in length. In one embodiment, peptides of the invention consist of about 10 to about 20 amino acids. In another embodiment, peptides of the invention consist of about 10 to about 15 amino acids. All longer and shorter peptides are within the scope of the subject invention as long as the longer or shorter peptide retains substantially the same activity in blocking or inhibiting autophosphorylation of a protein kinase as the peptides exemplified herein. The subject invention also concerns polypeptides that comprise a peptide sequence of the present invention, or a fragment or variant of that sequence, and that are able to block autophosphorylation of protein kinases, such as JAK2 and EGFR.

Peptides having substitution of amino acids other than those specifically exemplified in the subject peptides are also contemplated within the scope of the present invention. For example, non-natural amino acids can be substituted for the amino acids of a peptide of the invention, so long as the peptide having substituted amino acids retains substantially the same autophosphorylation inhibiting activity as the peptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a peptide having an amino acid of one class is replaced with another amino acid of the same class fall within the scope of the subject invention so long as the peptide having the substitution still retains substantially the same biological activity as a peptide that does not have the substitution. Table 1 below provides a listing of examples of amino acids belonging to each class.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Single letter amino acid abbreviations are defined in Table 2.

TABLE 2

| Letter Symbol | Amino Acid |
|---|---|
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |

TABLE 2-continued

| Letter Symbol | Amino Acid |
| --- | --- |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The peptides of the present invention can be formulated into pharmaceutically-acceptable salt forms. Pharmaceutically-acceptable salt forms include the acid addition salts and include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable base addition salts include sodium, potassium, calcium, ammonium, and magnesium salts. Pharmaceutically-acceptable salts of the peptides of the invention can be prepared using conventional techniques.

The subject invention also concerns polynucleotides that encode the peptides of the invention. Methods and materials for synthesizing and preparing a polynucleotide encoding a peptide of the invention are well known in the art. Because of the degeneracy of the genetic code, a variety of different polynucleotide sequences can encode a peptide of the present invention. In addition, it is well within the skill of a person trained in the art to create alternative polynucleotide sequences encoding the same, or essentially the same, peptides of the subject invention. These variant or alternative polynucleotide sequences, and the peptides encoded thereby, are within the scope of the subject invention. As used herein, references to "essentially the same" sequence refers to sequences which encode amino acid substitutions, deletions, additions, and/or insertions which do not materially alter the functional activity of the peptide encoded by the polynucleotides of the present invention. Variant peptides having amino acid substitutions, deletions, additions, and/or insertions which do not materially alter the functional activity of the peptide to block or inhibit autophosphorylation can also be prepared using standard techniques known in the art, and such variant peptides are encompassed within the scope of the present invention. Polynucleotide sequences encoding a peptide of the invention can be selected based on preferred codon usage of the animal in which it is to be administered. For example, if the peptide is to be administered to a human, the polynucleotide sequence can be selected for preferred codon usage in human cells.

The subject invention also concerns polynucleotide expression constructs that comprise a polynucleotide of the present invention comprising a nucleotide sequence encoding a peptide of the present invention. In one embodiment, the polynucleotide encodes a peptide comprising the amino acid sequence shown in SEQ ID NO. 1, or a fragment or variant thereof that can bind to an autophosphorylation site of a protein kinase, such as a JAK or EFGR, and inhibit autophosphorylation of the kinase.

As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a promoter sequence operably linked to a polynucleotide sequence encoding a peptide of the invention. Promoters can be incorporated into a polynucleotide using standard techniques known in the art. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells. Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

For expression in prokaryotic systems, an expression construct of the invention can comprise promoters such as, for example, alkaline phosphatase promoter, tryptophan (trp) promoter, lambda $P_L$ promoter, β-lactamase promoter, lactose promoter, phoA promoter, T3 promoter, T7 promoter, or tac promoter (de Boer et al., 1983).

If the expression construct is to be provided in a plant cell, plant viral promoters, such as, for example, the cauliflower mosaic virus (CaMV) 35S (including the enhanced CaMV 35S promoter (see, for example U.S. Pat. No. 5,106,739)) or 19S promoter can be used. Plant promoters such as prolifera promoter, Ap3 promoter, heat shock promoters, T-DNA 1'- or 2'-promotor of *A. tumafaciens*, polygalacturonase promoter, chalcone synthase A (CHS-A) promoter from petunia, tobacco PR-1a promoter, ubiquitin promoter, actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Seed-specific promoters such as the promoter from a β-phaseolin gene (of kidney bean) or a glycinin gene (of soybean), and others, can also be used. Constitutive promoters (such as the CaMV, ubiquitin, actin, or NOS promoter), tissue-specific promoters (such as the E8 promoter from tomato), developmentally-regulated promoters, and inducible promoters (such as those promoters than can be induced by heat, light, hormones, or chemicals) are contemplated for use with the polynucleotides of the invention.

Expression constructs of the invention may optionally contain a transcription termination sequence, a translation termination sequence, signal peptide sequence, and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Targeting a peptide to an intended cellular and/or extracellular destination through the use of operably linked signal peptide sequence is contemplated for use with the peptides of the invention. Chemical enhancers are cis-acting elements that increase gene transcription and can also be included in the expression construct. Chemical enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

Polynucleotides, vectors, and expression constructs of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides and peptides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis, T. et al., 1982). As used herein, "stringent" conditions for hybridization refers to conditions wherein hybridization is typically carried out overnight at 20–25 C. below the melting temperature (Tm) of the DNA hybrid in 6×SSPE, 5×Denhardt's solution, 0.1% SDS, 0.1 mg/ml denatured DNA. The melting temperature is described by the following formula (Beltz, G. A. et al., 1983):

Tm=81.5 C+16.6 Log[Na+]+0.41(% G+C)–0.61(% formamide)–600/length of duplex in base pairs.

Washes are typically carried out as follows:

(1) Twice at room temperature for 15 minutes in 1×SSPE, 0.1% SDS (low stringency wash).

(2) Once at Tm–20 C. for 15 minutes in 0.2×SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both the DNA strand sequence that is transcribed into RNA and the RNA sequence that is translated into protein. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the exemplified sequences. The polynucleotide includes both the sense and antisense strands as either individual strands or in the duplex.

The subject invention also concerns non-peptide compounds (peptidomimetics) that mimic the function of peptides of the present invention. Methods for preparing peptidomimetics based on structural features of the amino acid sequence of a peptide that pertain to functional or binding properties are known in the art.

The subject invention also concerns antibodies that bind to and block an autophosphorylation site on a protein kinase, such as a tyrosine kinase. In a specific embodiment, this autophosphorylation site is on a human JAK or EGFR polypeptide. In one embodiment, an antibody of the invention binds to an autophosphorylation site comprising the sequence LPQDKEYYKVKEP (SEQ ID NO. 2), or a fragment or variant thereof. Antibodies contemplated within the scope of the invention include both polyclonal and monoclonal antibodies. Preferably, the antibody is a monoclonal antibody, or an antigen binding fragment thereof. Antigen binding fragments include, but are not limited to, F(ab')$_2$, Fab', Fab, and Fv, and can be prepared using standard methods known in the art. The antibody can be derived from any animal capable of producing antibodies to an autophosphorylation epitope, and include, for example, primate, mouse, rat, goat, sheep, pig, and cow. Preferably, if the antibody is to be administered to humans, the antibody is a human antibody or is a "humanized" antibody derived from a non-human animal. Methods for humanizing non-human antibodies are known in the art and have been described in U.S. Pat. Nos. 5,530,101; 5,585,089; 5,693,762; 6,180,370; and 6,407,213. Antibodies of the invention can be prepared using standard techniques known in the art. In one embodiment, antibodies are prepared by immunizing an animal with a tyrosine kinase comprising an autophosphorylation site, or an immunogenic fragment thereof. Preferably, the tyrosine kinase is a JAK or EGFR tyrosine kinase. In one embodiment, antibodies are prepared by immunizing an animal with a peptide or polypeptide comprising the sequence LPQDKEYYKVKEP (SEQ ID NO. 2). Means for increasing immunogenicity of a peptide used to induce antibodies, such as conjugating it to a carrier moiety, such as keyhole limpet hemocyanin (KLH), ovalbumin, or albumin, are known in the art. Monoclonal antibodies can be prepared using standard methods known in the art (Kohler et al., 1975).

The subject invention also concerns methods for inhibiting the function and/or growth and replication of a cell that is expressing a protein kinase, and in particular, a tyrosine kinase polypeptide, such as a JAK or an EGFR tyrosine kinase, and whose function and/or activity is dependent upon the ability of the tyrosine kinase to autophosphorylate itself. The tyrosine kinase can be, for example, JAK2, erbB-1, erbB-2, erbB-3, or erbB-4. In one embodiment, the method comprises contacting a cell with a peptide, polynucleotide, peptidomimetic, and/or antibody of the invention. Peptides, polynucleotides, peptidomimetics, and/or antibodies of the invention can be delivered to a cell either through direct contact of peptide with the cell or via a carrier means. Carrier means for delivering compositions to cells are known in the art and include encapsulating the composition in a liposome moiety, and attaching the peptide or antibody to a protein or nucleic acid that is targeted for delivery to the target cell. Published U.S. patent application Nos. 20030032594 and 20020120100 disclose amino acid sequences that can be coupled to another peptide, protein, or nucleic acid and that allows the peptide, protein, or nucleic acid to be translocated across biological membranes. Published U.S. patent application No. 20020035243 also describes compositions for transporting biological moieties, such as peptides and proteins across cell membranes for intracellular delivery. Peptides can also be delivered using a polynucleotide that encodes a subject peptide. The polynucleotide is delivered to the cell where it is taken up and the polynucleotide is transcribed into RNA and the RNA is translated into the encoded peptide.

The subject invention also concerns methods for treating autoimmune, inflammatory or oncological disorders in a patient wherein the inflammatory or oncological disorder is associated with the expression of a protein kinase, and in particular, a tyrosine kinase, such as a JAK tyrosine kinase or an EGFR, whose function and/or activity is dependent upon the ability of the tyrosine kinase to autophosphorylate itself. The tyrosine kinase can be, for example, JAK2, erbB-1, erbB-2, erbB-3, or erbB-4, or the equivalent thereof in a particular animal species. In one embodiment, an effective amount of a peptide, polynucleotide, peptidomimetic, or antibody of the present invention is administered to a patient having an autoimmune, inflammatory or oncological disorder and who is in need of treatment thereof. The patient can be a human or other mammal, such as a dog, cat, or horse, or other animals having the inflammatory or oncological disorder. Means for administering and formulating peptides, polynucleotides, peptidomimetics, and antibodies for administration to a patient are known in the art, examples of which are described herein. Peptides can also be delivered using a polynucleotide that encodes a subject peptide. Any polynucleotide having a nucleotide sequence that encodes a peptide of the invention is contemplated within the scope of the invention. The polynucleotide is delivered to the cell where it is taken up and the polynucleotide is transcribed into RNA and the RNA is translated into the encoded peptide. Autoimmune and inflammatory disorders associated with the expression of an autophosphorylating tyrosine kinase include arthritis, multiple sclerosis, lupus, Crohn's disease, diabetes, graft rejection, and related neurological and inflammatory connective tissue diseases (e.g., Sjögren's syndrome). Specifically contemplated within the scope of the present invention is treatment and/or prevention of cardiovascular disease and disorders, such as coronary heart disease, that are associated with the presence of an inflammatory condition. Oncological disorders associated with the expression of an autophosphorylating tyrosine kinase include cancer and/or tumors of the breast, kidney, mouth, larynx, esophagus, stomach, colon, ovary, lung, bladder, skin, muscle, pancreas, prostate, blood cells, and brain. Brain tumors contemplated for treatment within the scope of the invention include glioblastomas. An oncological disorder specifically contemplated within the scope of the present methods is leukemia. In one embodiment, the leukemia is a type associated with chromosomal rearrangements that deregulate and/or result in constitutively active autophosphorylation of a protein kinase.

For the treatment of oncological disorders, the peptides, peptidomimetics, and antibodies of this invention can be administered to a patient in need of treatment in combination with other antitumor substances or with radiation therapy or with surgical treatment to remove a tumor. These other substances or radiation treatments may be given at the same or different times as the peptides, polynucleotides, peptidomimetics, and antibodies of this invention. For example, the peptides, polynucleotides, peptidomimetics, and antibodies of the present invention can be used in combination with mitotic inhibitors such as taxol or vinblastine, alkylating agents such as cisplatin, cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other drugs or antibodies that inhibit functions of tyrosine kinases, such as, for example, GLEEVEC and HERCEPTIN, respectively.

In one embodiment, one or more of the peptides of the subject invention can be provided in the form of a multiple peptide construct. Such a construct can be designed so that multiple peptides are linked to each other by intervening moieties wherein the intervening moieties are subsequently cleaved or removed following administration of the multiple peptide construct to a patient. Methods for constructing multiple peptide constructs are known in the art. For example, peptides of the present invention can be provided in the form of a multiple antigenic peptide (MAP) construct. The preparation of MAP constructs has been described in Tam (1988). MAP constructs utilize a core matrix of lysine residues onto which multiple copies of an immunogen are synthesized. Multiple MAP constructs, each containing different peptides, can be prepared and administered in accordance with methods of the present invention. In another embodiment, a multiple peptide construct can be prepared by preparing the subject peptides having at least one metal chelating amino acid incorporated therein, preferably at the amino and/or carboxy terminal of the peptide as described, for example, in U.S. Pat. No. 5,763,585. The peptides are then contacted with a solid support having attached thereto a metal ion specific for the metal chelating amino acid of the peptide. A multiple peptide construct of the invention can provide multiple copies of the exact same peptide, including variants or fragments of a subject peptide, or copies of different peptides of the subject invention.

Therapeutic application of the subject peptides, polynucleotides, peptidomimetics, and antibodies, and compositions containing them, can be accomplished by any suitable therapeutic method and technique presently or prospectively known to those skilled in the art. The peptides, polynucleotides, peptidomimetics, and antibodies can be administered by any suitable route known in the art including, for example, oral, nasal, rectal, parenteral, subcutaneous, or intravenous routes of administration. Administration of the peptides, polynucleotides, peptidomimetics, and antibodies of the invention can be continuous or at distinct intervals as can be readily determined by a person skilled in the art.

Compounds and compositions useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive peptide, antibody, or peptidomimetic is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptide, antibody, or peptidomimetic of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptide, antibody, or peptidomimetic based on the weight of the total composition including carrier or diluent.

The compounds and molecules of the subject invention can also be administered utilizing liposome technology, slow release capsules, implantable pumps, and biodegradable containers. These delivery methods can, advantageously, provide a uniform dosage over an extended period of time.

The subject peptides and antibodies can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides known in the art (see, for example, U.S. Pat. No. 4,179,337). The subject peptides and antibodies can also be modified to improve cell membrane permeability. In one embodiment, cell membrane permeability can be improved by attaching a lipophilic moiety, such as a steroid, to the peptide or antibody. Other groups known in the art can be linked to peptides and antibodies of the present invention.

The subject invention also concerns a packaged dosage formulation comprising in one or more containers at least one peptide, polynucleotide, peptidomimetic, or antibody of the subject invention formulated in a pharmaceutically acceptable dosage. The package can contain discrete quantities of the dosage formulation, such as tablet, capsules, lozenge, and powders. The quantity of peptide, polynucleotide, peptidomimetic, and/or antibody in a dosage formulation and that can be administered to a patient can vary from about 1 mg to about 2000 mg, more typically about 1 mg to about 500 mg, or about 5 mg to about 250 mg, or about 10 mg to about 100 mg.

The subject application also concerns methods for screening for compounds that inhibit autophosphorylation activity of a tyrosine kinase. In one embodiment, a compound to be tested is contacted with an amino acid sequence comprising a site of autophosphorylation of a tyrosine kinase and determining if the test compound binds to the site. In a specific embodiment, the site comprises the amino acid sequence LPQDKEYYKVKEP (SEQ ID NO. 2). Compounds that inhibit autophosphorylation can be selected for further evaluation.

The subject invention also concerns kits comprising in one or more containers a composition, compound, or molecule of the present invention. In one embodiment, a kit contains a peptide, polynucleotide, peptidomimetic, and/or antibody of the present invention. In a specific embodiment, a kit comprises a peptide having the amino acid sequence shown in SEQ ID NO. 1, SEQ ID NO. 37, or SEQ ID NO. 72, or a fragment or variant of the peptide that can bind to an autophosphorylation site of a protein kinase, such as JAK2 or EGFR, and thereby inhibit autophosphorylation of the protein kinase. In a more specific embodiment, a kit comprises a peptide consisting of the amino acid sequence shown in SEQ ID NO. 1, SEQ ID NO. 37, or SEQ ID NO. 72.

The subject invention also concerns methods for preparing a peptide, polynucleotide or antibody of the invention. In one embodiment, a peptide or polynucleotide of the invention is chemically synthesized using standard methods. In another embodiment, a peptide or antibody of the invention is prepared by expressing a polynucleotide encoding the peptide or antibody either in vitro or in vivo and then isolating the expressed peptide or antibody.

The subject invention also concerns methods for negatively regulating signaling pathways mediated by cytokine binding comprising administering to an animal or contacting a cell with an effective amount of a peptide, polynucleotide, peptidomimetic and/or antibody of the present invention. In one embodiment, the cytokine is IFN-γ. In one embodiment, the signaling pathway comprises intracellular STAT1α, which is activated by phosphorylation of STAT1α. The compounds and molecules of the invention can be used to inhibit phosphorylation of STAT1α.

All patents, patent applications, provisional applications, and publications referred to or cited herein are incorporated by reference in their entirety, including all figures and tables, to the extent they are not inconsistent with the explicit teachings of this specification.

MATERIALS AND METHODS

Cell culture and virus: All cell lines were from American Type Culture Collection (ATCC, Manassas, Va.). WEHI-3 murine macrophages were maintained in Dulbecco's modified Eagle's medium (DMEM, Sigma, St. Louis, Mo.) supplemented with 10% fetal bovine serum (Hyclone, Logan, Conn.), 100 units/ml penicillin, 100 μg/ml streptomycin, and 0.05 M β-mercaptoethanol. WISH human fibroblast cells were maintained in Eagles minimum essential medium (EMEM, JHR Biosciences, Lenexa, Kans.) supplemented with 10% fetal bovine serum, 100 units/ml penicillin, and 100 μg/ml streptomycin (complete media) in 6-well tissue culture plates at 37° C. in a 5% $CO_2$ atmosphere. Bovine aortic endothelial cells (BAECs) were generously provided by Dr. Richard J. Johnson and Dr. Takahiko Nakagawa of the Division of Nephrology, College of Medicine, University of Florida. BAEC culture reagents were purchased from Cambrex (Walkersville, Md.). BAECs were cultured according to the manufacturer's instructions in 6-well tissue culture plates at 37° C. in a 5% $CO_2$ atmosphere. Starvation media contains EMEM without antibiotics or F12K media supplemented with 100 units/ml penicillin and 100 μg/ml streptomycin. Encephalomyocarditis virus (EMCV) was obtained from ATCC and stored at −70° C. until use.

Reagents: Recombinant human JAK2 immobilized on agarose beads, human EGFR isolated from A431 cells, and recombinant human Src were purchased from Upstate Biotechnology, Lake Placid, N.Y. The EGFR was supplied precomplexed with its ligand, EGF. An assay kit for measuring Src kinase activity was also purchased from Upstate Biotechnology. The assay kit included the Src substrate peptide and the Src assay buffer. Recombinant human VEGFR (vascular endothelial growth factor receptor) was purchased from Calbiochem, San Diego, Calif. [γ-$^{32}$P]ATP was from Amersham Biosciences.

Peptides: The peptides used in the current study are listed in Table 3, and are synthesized in our laboratory on a Perseptive Biosystems 9050 automated peptide synthesizer using conventional fluorenylmethyloxycarbonyl (Fmoc) chemistry as described previously (Szente et al., 1996). The addition of a lipophilic group (palmitoyl-lysine) to the N-terminus of a synthetic peptide was performed as the last step using a semi-automated protocol as previously described. Peptides were characterized by mass spectrometry and purified by high performance liquid chromatography (HPLC). Peptides were dissolved in either deionized water, or dimethyl sulfoxide (Sigma, St. Louis, Mo.).

Binding assays: For ELISA binding assays Tkip and other peptides to be tested were bound to 96-well plates in 0.1 M carbonate binding buffer (pH 9.6) at a final concentration of 3 μg/well (50 μl). Wells were then washed three times with wash buffer containing 0.9% NaCl and 0.05% tween-20 in PBS and blocked with 2% gelatin and 0.05% tween-20 in PBS for 1 h at room temperature. Wells were then washed three times with wash buffer and incubated with various concentrations of biotinylated JAK2 WT peptide and biotinylated P-JAK2 WT peptide for 1 h at room temperature in blocking buffer. Following incubation, wells were washed five times with wash buffer to remove any unbound biotinylated peptides. Bound biotinylated peptides were detected by incubation with a 1:500 dilution of NEUTRAVIDIN biotin binding-protein conjugated with horseradish peroxidase (Molecular Probes, Eugene, Oreg.) in blocking buffer for 1 h at room temperature. Wells were then washed five times with wash buffer and developed with a solution of o-phenylenediamine (OPD) in stable peroxidase buffer (Pierce, Rockford, Ill.). The assay was stopped with the addition of 2 M $H_2SO_4$ (50 μl) to each well. Absorbance was measured using a 450 microplate reader (Bio-rad, Hercules, Calif.) at 490 nm. Control experiments were carried out as described above in the absence of immobilized peptides.

Peptide competition experiments were conducted using peptides derived from the JAK tyrosine kinase family, vascular endothelial growth factor receptor (VEGFR), and cyclin dependent kinase (CDK) to compete with biotinylated JAK2 WT peptide for binding to Tkip. Binding of biotinylated JAK2 WT was determined as above, except that following Tkip peptide immobilization, washing, and blocking in blocking buffer for 1 hr at room temperature unlabeled competitors were added to wells and incubated for 30 min at varying concentrations before biotinylated JAK2 WT peptide was incubated for 1 hr in each well to determine the extent of competition with unlabeled peptides. Detection and analysis of binding was carried out as described above.

Immunoblot Analysis: WISH fibroblast cells were plated in 6-well plates at a cell density of $3 \times 10^6$ cells/well. After overnight incubation with complete culture media, WISH cells were incubated in starvation medium for 17 hours and pretreated with complete culture media or different concentrations of Tkip (8 μM or 1 μM) for an additional 17 hours at 37° C. in a 5% $CO_2$ atmosphere. WISH cells were then incubated in the presence or absence or 5000 U/ml IFN-γ (PBL Biomedical Laboratories, Piscataway, N.J.) to activate the JAK-STAT pathway. Fibroblast cells were washed twice in cold phosphate buffered saline (PBS) to remove media and cell debris. Cell lysates were prepared by adding 200 μl of cold lysis buffer (50 mM Tris-HCl [pH 7.4], 0.25 M NaCl, 2 mM EGTA, 2 mM EDTA, 50 mM NaF, 2 mM $Na_3VO_4$, 2 mM DTT, 20 mM β-glycerophosphate, 1 mM PMSF, 10% glycerol, 10 μg/ml leupeptin, 10 μg/ml aprotinin, 10 μg/ml pepstatin, 0.25% sodium deoxycholate, 1% NP-40, and 0.1% SDS) to each well. Lysis was allowed to proceed for 1 hr at 4° C. (rocking) to ensure complete lysis. Lysates were then centrifuged to remove cell debris and the supernatant was transferred to a fresh microcentrifuge tube. Samples containing lysate, lysis buffer, and sample buffer were boiled for 5 min and pulsed centrifuged. Protein lysates were resolved by sodium dodecyl sulfate-polyacrylamide gel electrophoresis (SDS-PAGE) on a 12% polyacrylamide gel (Biorad, Richmond, Calif.). Proteins were then transferred to nitrocellulose membranes (Amersham Biosciences) overnight at low voltage. To reduce nonspecific binding, membranes were incubated in blocking buffer containing 5% nonfat dry milk in PBS for 1 hr at room temperature and washed in wash buffer containing 1% nonfat dry milk and 0.1% Tween-20 in PBS (PBST) three times. To detect phosphorylated STAT1α, membranes were incubated with antibodies to tyrosine-phosphorylated STAT1α (Cell Signaling Technologies, Beverly, Mass.) phosphorylated at tyrosine residue 701 (1:100) in wash buffer overnight with agitation at 4° C. After three washes in PBST, membranes were incubated in HRP-conjugated goat anti-rabbit IgG secondary antibodies (Santa Cruz, Santa Cruz, Calif.) at a dilution of 1:5000 in wash buffer for 1 hr at room temperature. Following three washes in wash buffer, membranes were incubated for 1 min with enhanced chemiluminescence detection reagents (Amersham) and exposed to photographic film to visualize protein bands.

Flow Cytometry: WISH fibroblast cells ($2 \times 10^6$) were incubated for 48 h with media alone, 25 µM MuIFNγ (95–125) peptide, or lipophilic Tkip (LT) at varying concentrations (1 µM, 10 µM, 25 µM) in the presence or absence of 5000 units/ml IFN-γ in 6-well culture plates at 37° C. in a 5% $CO_2$ atmosphere. Following incubation, cells were washed twice with PBS and harvested by trypsinization into two sets of 5-ml round bottom polystyrene tubes (Fisher, Pittsburgh, Pa.) and washed twice with PBS. For cell surface staining a direct immunofluorescence protocol was employed. Briefly, cells were incubated on ice with a 100 µl staining solution in PBS of either anti-human MHC class I monoclonal antibody conjugated to R-phycoerythrin (R-PE, 1:100) or with monoclonal mouse IgG2a antibody conjugated to R-PE (1:100) as an isotype control for 1 h at room temperature in the absence of light. The fluorescent-conjugated isotype antibody was used to determine background fluorescence by identifying nonspecific binding of the monoclonal antibody to WISH cells. The above antibodies were purchased commercially from Ancell Corporation (Bayport, Minn.). Following incubation, cells were then washed three times with PBS to remove unbound antibody molecules. WISH fibroblast cells were finally resuspended in 500 µl of PBS and analyzed on a FACScan fluorescence-activated cell sorter (Becton Dickinson, San Jose, Calif.). The apparatus was equipped with an argon laser. The red fluorescence of R-PE was excited at 488 nm. Cell debris was isolated from intact cells by performing forward and side scatter analysis on each sample and therefore excluded from the analysis. The fluorescence intensity of the negative controls were subtracted from the mean fluorescence for the R-PE labeled cells. For each sample 10,000 stained cells were examined. Flow cytometry data were analyzed using CellQuest analysis software (Becton Dickinson, San Jose, Calif.).

Immunoprecipitation: Bovine aortic endothelial cells were plated at a density of $3 \times 10^6$/well in 6-well plates and allowed to incubate for 10 hrs at 37° C. Growth media was then removed and replaced with growth media with or without peptides at the indicated concentrations overnight at 37° C. Cells were then treated with serum-free medium alone or serum-free medium containing peptides at the indicated concentrations for 2 hrs. BAECs were then incubated in the presence or absence of 50 ng/ml VEGF (Upstate Biotechnology, Lake Placid, N.Y.) in serum-free media for 10 min and lysed with 500 µl lysis buffer. Cells were lysed in lysis buffer containing 50 mM Tris-HCl [pH 7.4], 0.25 M NaCl, 2 mM EGTA, 2 mM EDTA, 50 mM NaF, 2 mM $Na_3VO_4$, 2 mM DTT, 20 mM β-glycerophosphate, 1 mM PMSF, 10% glycerol, 10 µg/ml leupeptin, 10 µg/ml aprotinin, 10 µg/ml pepstatin, 0.25% sodium deoxycholate, 1% NP-40, and 0.1% SDS for 1 hr at 4° C. while rotating. Lysates were microcentrifuged at 7,000×g at 4° C. for 15 min to remove cell debris and nuclei. Supernatants were transferred to a new microcentrifuge tube and incubated with 2 µg/ml anti-VEGFR-2 polyclonal antibody (Santa Cruz Biotechnology, Santa Cruz, Calif.) for 2 hrs at 4° C. while rotating. Protein G-Sepharose beads (40 µL, 1:1 slurry) were added to the supernatant and allowed to incubate for 1 hr at 4° C. while rotating. Following centrifugation to pellet the protein G immune complexes, supernatant was removed and discarded. The immune complexes were subsequently washed three times with lysis buffer and twice with PBS. For SDS-PAGE analysis, immune complexes were boiled (100° C.) in 35 µl of SDS sample buffer for 5 min and resolved on a 12% polyacrylamide gel. Following transfer to nitrocellulose membranes, membranes were blocked, washed, and treated with specific antibodies to detect phosphorylated tyrosine proteins (4G10, Upstate Biotechnology, Lake Placid, N.Y.) and VEGFR-2 proteins. Detection of proteins was accomplished using enhanced chemiluminescence protein detection reagents (Amersham).

Antiviral Assay: Antiviral activity was determined using a standard viral cytopathogenic effect assay described previously with minor modifications (Familletti et al., 1981). Antiviral assays were performed to evaluate the ability of Tkip to block antiviral activity mediated by IFN-γ. Briefly, WEHI-3 murine macrophage cells ($5 \times 10^5$) were incubated with either media alone, 2000 U/ml IFN-γ (PBL Biomedical Laboratories, Piscataway, N.J.), or both 2000 U/ml IFN-γ and 10 µM lipophilic Tkip for 24 h in 24-well plates (Becton Dickinson Labware, Franklin Lakes, N.J.) at 37° C. in a 5% $CO_2$ atmosphere. Following incubation, WEHI-3 cells were washed three times with growth media and infected with EMCV for 1 h at 37° C. EMCV was added at a multiplicity of infection (MOI) of 0.02. WEHI-3 cells were then washed three times to remove viral particles and incubated in fresh growth media for an additional 24 h at 37° C. Plates were subsequently blotted dry and stained with 0.1% crystal violet solution for 5 min to stain live cells. Unbound crystal violet was aspirated and the plates were thoroughly rinsed with deionized water, blotted, and allowed to air dry. Plates were then scanned using an Astra 2100U flatbed computer scanner (UMAX Technologies, Dallas, Tex.) and analyzed using ImageJ 1.29 software (NIH) to assess cell survival. Percentages of cell survival were determined by comparing experimental treatment groups with the virus only control group. Recombinant murine IFN-γ (specific activity $1 \times 10^7$ U/ml) used in the antiviral assay described above were obtained from PBL (Camarillo, Calif.).

In vitro Kinase Assays: Autophosphorylation activity of EGFR and VEGFR-1 was measured in a reaction mixture containing kinase buffer (20 mM Tris-HCl [pH 7.5], 2 mM dithioreitol, 50 mM potassium chloride, 0.3 mM sodium orthovanadate, 5 mM magnesium chloride, 10 mM glycerophosphate, 2 mM EGTA, 1 M manganese chloride), Tkip, substrates, and 5 µCi of [$^{32}$P]γ-ATP (specific activity 6000 Ci/mmol; 1 mCi=37 Mbq) (Amersham Biosciences, Piscataway, N.J.). EGFR and VEGFR in vitro kinase assays were carried out in 22.5 µL reaction volumes containing 10 µL Tkip, 2.5 µL substrates, and 10 µL [$^{32}$P]γ-ATP incubated at 30° C. for 10 min. EGFR (supplied precomplexed with EGF) was obtained from Upstate Biotechnology (Lake Placid, N.Y.). VEGFR and VEGF were obtained from Calbiochem (San Diego, Calif.) and Peprotech (Rocky Hill, N.J.), respectively.

Determination of JAK2 autophosphorylation activity was performed in reaction mixtures containing recombinant human JAK2 immobilized on agarose beads (Upstate Biotechnology, Lake Placid, N.Y.), 1 µCi/µl of [$^{32}$P]γ-ATP (Amersham Biosciences, Piscataway, N.J.), and either Tkip or JAK 2 WT peptide incubated in kinase buffer (10 mM HEPES [pH 7.4], 50 mM sodium chloride, 0.1 mM sodium orthovanadate, 5 mM magnesium chloride, 5 mM manganese chloride). JAK2 kinase assays were performed in 35 µL reaction volumes containing 10.5 µL Tkip, 20 µL JAK2 agarose beads, 1 µL sIFNGR-1, and 3.5 µL [$^{32}$P]γ-ATP incubated at 30° C. for 30 min with intermittent agitation. It was determined in our laboratory that addition of a mouse soluble IFNGR-1 subunit dramatically stimulated JAK2 kinase activity and, hence, was added at 2 µg per reaction. EGFR, VEGFR, and JAK2 kinase reactions were terminated with the addition of 5 µl 6×SDS sample buffer (0.5 M Tris-HCl [pH 6.8], 36% glycerol, 10% SDS, 9.3% DTT, 0.012% bromophenol blue). Incubation of JAK2 agarose beads in SDS sample buffer (100° C.) was designed to elute bound proteins from the agarose beads. The reaction mixtures were separated on a 10% SDS polyacrilamide gel. Autoradiography was used to determine phosphorylation activity.

Src kinase activity was performed with a Src substrate peptide (KVEKIGEGTYGVVYK) (SEQ ID NO. 73) using a Src kinase assay kit according to the manufacturer's specifications (Upstate Biotechnology, Lake Placid, N.Y.) according to the manufacturer's specifications. Briefly, Src substrate peptide was incubated in Src kinase buffer (100 mM Tris-HCl [pH 7.2], 125 mM $MgCl_2$, 25 mM $MnCl_2$, 2 mM EGTA, 0.02 mM $Na_3VO_4$, and 2 mM dithioreitol), 5 µCi of [$^{32}P$]γ-ATP (75 mM $MnCl_2$, 500 µM ATP), recombinant human Src (Upstate Biotechnology, Lake Placid, N.Y.), and Tkip, JAK2 WT peptide, or in the absence of peptide for 10 min at 30° C. Reaction mixtures were spotted on P81 phosphocellulose discs (supplied with kit) to bind phosphorylated Src substrate peptide, washed three times for 5 min with 0.75% phosphoric acid, washed twice with acetone for 1 min, and placed in vials to which 4 ml of ScintiVerse® (Fisher, Pittsburgh, Pa.) was added. The phosphocellulose discs were analyzed using a liquid scintillation counter to measure $^{32}P$-labeled proteins. For comparison with Src, JAK2 was also assayed using the same procedure. The assay was setup as described above for the Src kinase assay. However, reactions were incubated in the presence of 2 mM dithioreitol in the buffer to release JAK2 from the agarose beads. Following the appropriate incubation period reactions were gently centrifuged. Supernatants were spotted on phosphocellulose discs and processed as above.

EXAMPLE 1

Binding of Tkip Peptide to Autophosphorylation Peptide Sequence

The autophosphorylation site of human JAK2 consists of residues $^{1001}$LPQDKEYYKVKEP (SEQ ID NO. 2) with $^{1007}$Y as the tyrosine autophosphorylation residue that results in activation of JAK2 (Yasukawa et al., 1999). A complementary peptide approach was used to develop a short peptide capable of binding to this site (Villain et al., 2000). The complementarity refers to the hydropathic complementarity, which has been shown empirically to result in peptide/peptide binding. Recently, an algorithm has been developed that specifies the "best" complementarity fit (Fassina et al., 1992). The sequences of several peptides that varied in their complementarity to $^{1001}$LPQDKEYYKVKEP (SEQ ID NO. 2) were generated. It was discovered that the best complementary fit did not necessarily result in the best binding to JAK2 peptide (data not shown). Thus, the best binding, which was not the best complementary fit, occurred with complementary peptide WLVFFVIFYFFR (SEQ ID NO. 1). This peptide was developed by reading the complementary strand codons in the JAK2 autophosphorylation site in the 5'-3' direction (Blalock et al., 1986). Data on binding of WLVFFVIFYFFR (SEQ ID NO. 1) to $^{1001}$LPQDKEYYKVKEP (SEQ ID NO. 2), as determined by ELISA are presented in FIG. 1. Peptide sequences are presented in Table 3.

TABLE 3

Amino Acid Sequences of Peptides

| Peptide[a] | Sequence | |
|---|---|---|
| Tkip | WLVFFVIFYFFR | (SEQ ID NO. 1) |
| JAK2 WT | $^{1001}$LPQDKEYYKVKEP | (SEQ ID NO. 2) |
| p-JAK2 WT | $^{1001}$LPQDKE☐YKVKEP | (SEQ ID NO. 2) |
| VEGFR | $^{1208}$SSDVRYVNAFKFM | (SEQ ID NO. 74) |
| CDK-2 cyclin box | $^{41}$KTEGVPSTAIREISLLKELNH | (SEQ ID NO. 75) |
| MuIFN-γ(95-125) | $^{95}$AKFEVNNPQVQRQAFNELIRVVHQLLPESSL | (SEQ ID NO. 76) |

[a]Peptides were synthesized as described in Materials and Methods.
Murine IFN-γ sequence is derived from the mature form. Lipophilic group and biotinylated modifications were added to the N-terminus of the peptide. Tyrosines targeted for phosphorylation are indicated in bold.
Tkip = tyrosine kinase inhibitor peptide,
JAK2 = Janus Kinase 2,
WT = wild type,
p = phosphorylated,
VEGFR = vascular endothelial growth factor receptor,
CDK = cyclin dependent kinase.
The square denotes the phosphotyrosine moiety. The JAK2 WT sequence is the same for both mice and humans.

Unless otherwise stated the peptides used in the kinase reactions described above were used at 50 µM. Immunoblotting was performed in parallel to determine protein levels used in the kinase reactions. Dose response kinase activity studies of JAK2 and EGFR were performed as described above.

Following are examples which illustrate procedures for practicing the invention. These examples should not be construed as limiting. All percentages are by weight and all solvent mixture proportions are by volume unless otherwise noted.

Biotinylated JAK2 autophosphorylation peptide (biotinylated JAK2 WT) was added at different concentrations to solid-phase complementary peptide, designated tyrosine kinase inhibitory peptide Tkip, as well as to solid-phase control peptides. These control peptides consisted of IFN-γ sequence 95–125 (IFN-γ95–125) (SEQ ID NO. 76), cyclin-dependent kinase, cyclin box peptide 41–61 (CDK 41–61) (SEQ ID NO. 75), and vascular endothelial growth factor receptor autophosphorylation peptide VEGFR 1208–1222 (SEQ ID NO. 74). As shown in FIG. 1A, JAK2 WT peptide bound only to Tkip peptide in a dose-dependent manner.

Figure 1B:
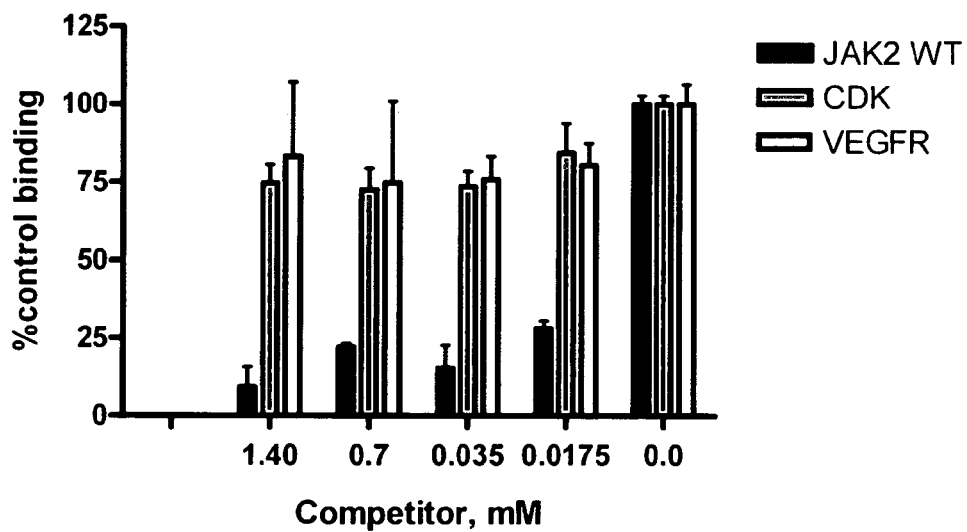

Binding to the control peptides was negligible. In ELISA competitions, JAK2 WT peptide but neither CDK 41–61 nor VEGFR 1208–1222, inhibited biotinylated JAK2 WT peptide binding to Tkip peptide (FIG. 1B). The binding data suggest that the Tkip peptide specifically recognized JAK2 WT.

EXAMPLE 2

Peptide Inhibition of Tyrosine Kinase Autophosphorylation

Figure 2A:
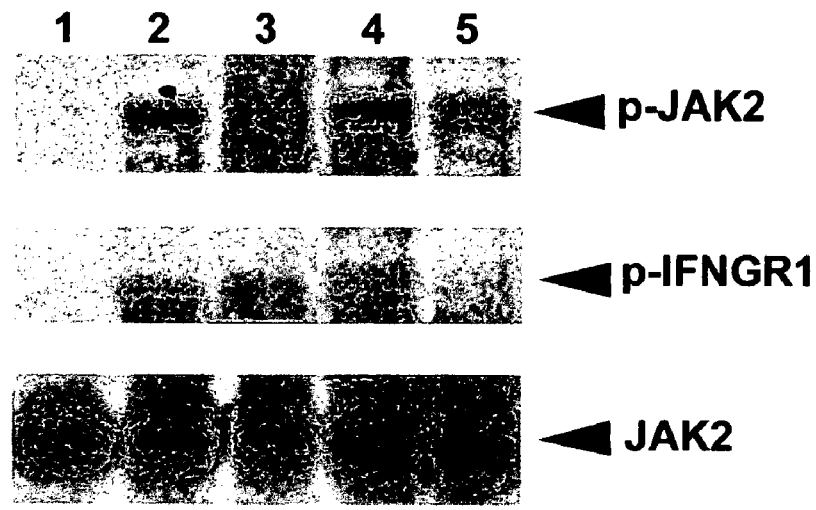
FIGS. 2A–2F show kinase inhibitory specificity of Tkip peptide.

Experiments were conducted to determine whether Tkip peptide could inhibit JAK2 autophosphorylation as well as phosphorylation of IFN-γ receptor subunit IFNGR-1. As shown in FIG. 2A, Tkip at 50 μM inhibited both the autophosphorylation of JAK2 as well as JAK2 phosphorylation of IFNGR-1. A control peptide, JAK2 WT, at the same concentration had no effect on JAK2-induced tyrosine phosphorylations. Thus, consistent with Tkip binding to JAK2 WT, it also inhibited JAK2 autophosphorylation as well as JAK2 phosphorylation of IFNGR-1.

Figure 2B:
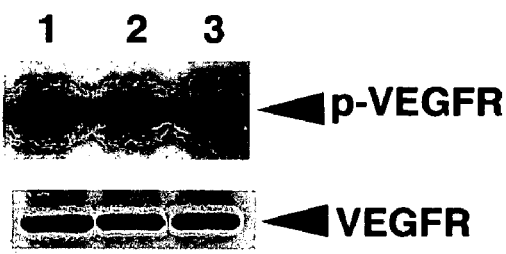
Figure 2C:
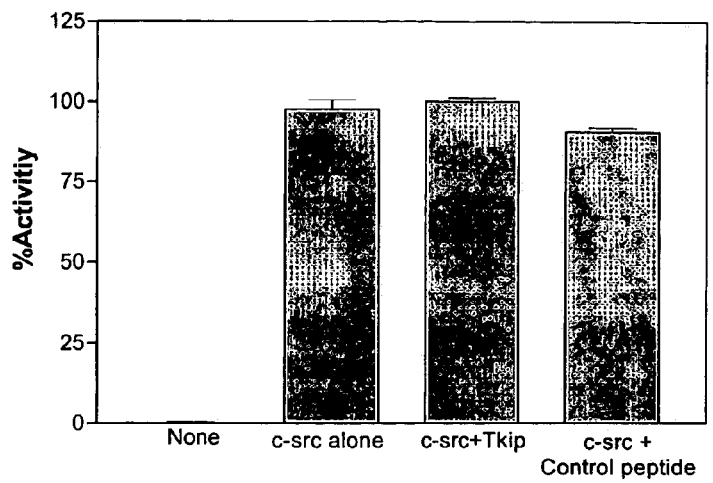
Figure 2D:
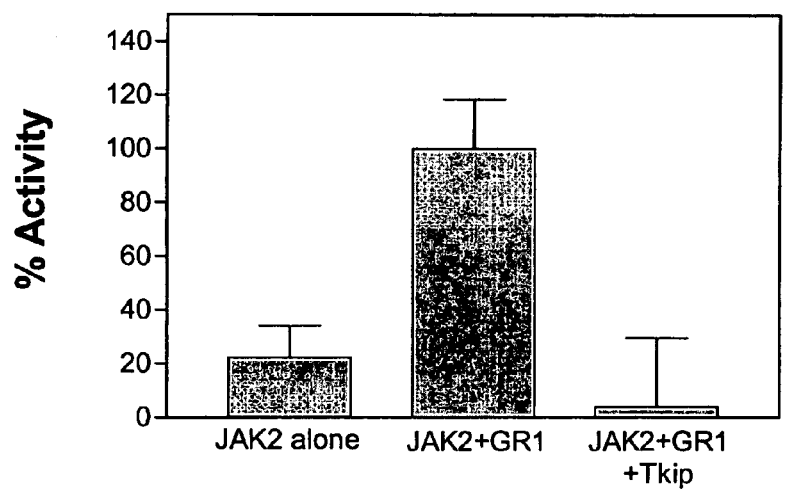
Figure 2E:
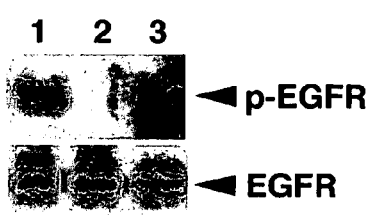
Figure 2F:
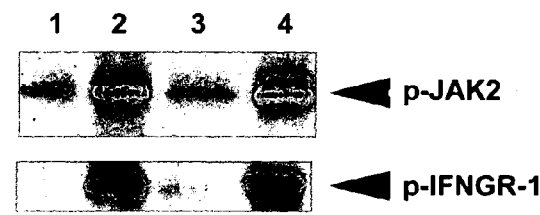

Tkip peptide was also tested for its inhibitory effects against several other tyrosine kinases. VEGFR is involved in the development and growth of the vascular endothelial system (Ferrara et al., 2003). As shown in FIG. 2B, Tkip peptide at 50 μM did not inhibit the autophosphorylation of VEGFR, but under the same conditions completely inhibited JAK2 autophosphorylation as well as JAK2 phosphorylation of IFNGR-1 (FIG. 2F). Thus, compared to VEGFR, Tkip shows specificity toward JAK2.

Tkip peptide was also tested against a nonautophosphorylation tyrosine kinase, c-src. As shown in FIG. 2C, Tkip at 50 μM failed to inhibit c-src phosphorylation of a protein substrate. By contrast, Tkip significantly blocked JAK2 autophosphorylation/IFNGR-1 phosphorylation as estimated by greater than 95% inhibition of $^{32}P$ incorporation into JAK2/IFNGR-1 (FIG. 2D). Thus, the data on Tkip failure to block VEGFR and c-src tyrosine phosphorylations are evidence of specificity of Tkip for inhibition of JAK2 autophosphorylation via interaction with the JAK2 autophosphorylation site.

Interaction of Tkip with the JAK2 autophosphorylation site and inhibition of JAK2 function raises the question of possible functional relationship of Tkip to a group of regulators called suppressors of cytokine signaling or SOCS. SOCS are recently discovered negative regulators of cytokine, growth factors, and hormone signaling (Hanada et al., 2003; Kile et al., 2002; Alexander 2002; Larsen et al., 2002). Currently, there are eight identified members of the SOCS family, SOCS-1 to SOCS-7 and CIS. SOCS-1 and SOCS-3 are the negative regulators of both JAK2 and the epidermal growth factor receptor (EGFR) (Hanada et al., 2003; Kile et al., 2002; Alexander 2002; Larsen et al., 2002; Xia et al., 2002). EGFR autophosphorylation is complex with up to five autophosphorylation sites (Wells 1999). Experiments were conducted to determine whether Tkip could inhibit EGFR tyrosine kinase activity. As shown in FIG. 2E, Tkip at 50 μM completely inhibited EGFR autophosphorylation. For comparison, Tkip also inhibited JAK2 autophosphorylation as well as JAK2 phosphorylation of IFNGR-1 (FIG. 2F). Thus, Tkip inhibited EGFR autophosphorylation, which is consistent with its specificity for the SOCS-1 and SOCS-3 autophosphorylation sites of JAK2 and EGFR.

EXAMPLE 3

Tkip Peptide Dose-Dependent Inhibition of JAK2 and EGFR Autophosphorylation

Figure 3A:
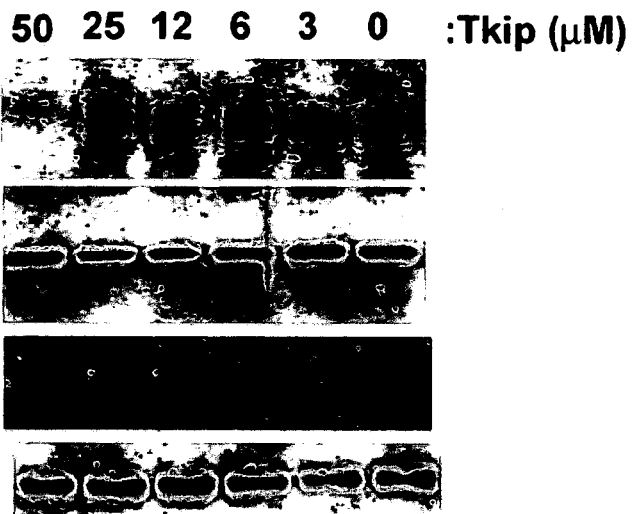
FIGS. 3A and 3B show dose response of Tkip peptide inhibition of JAK2, IFNGR-1, and EGFR autophosphorylation in vitro.
Figure 3B:
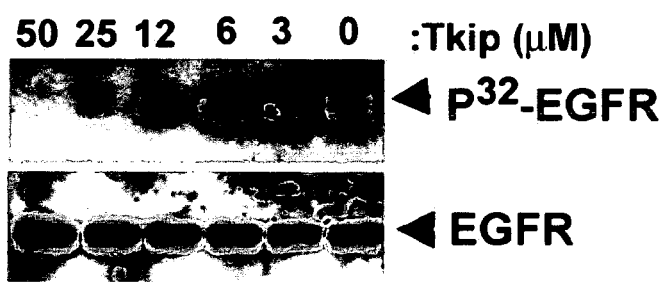

Tkip inhibition of JAK2 and EGFR autophosphorylation was compared in a dose-response study. As shown in FIG. 3, Tkip peptide similarly inhibited autophosphorylation of JAK2 (FIG. 3A) and EGFR (FIG. 3B) with 25 to 50 μM significantly blocking JAK2 autophosphorylation and 12 to 25 μM blocking IFNGR-1 phosphorylation by JAK2, while 6 to 12 μM significantly blocked EGFR phosphorylation. Thus, the patterns of dose-response inhibition of JAK2 and EGFR were similar. It is of interest that Tkip inhibited JAK2 phosphorylation of IFNGR-1 at a lower concentration than that for JAK2 autophosphorylation itself. This suggests that Tkip can block JAK2 phosphorylation of a substrate (IFNGR-1) more effectively than the autophosphorylation of JAK2, and that Tkip binds phosphorylated JAK2 more effectively than it does unphosphorylated JAK2.

EXAMPLE 4

Tkip Peptide Binding to Unphosphorylated Vs. Phosphorylated JAK2 WT Peptide

Figure 4:
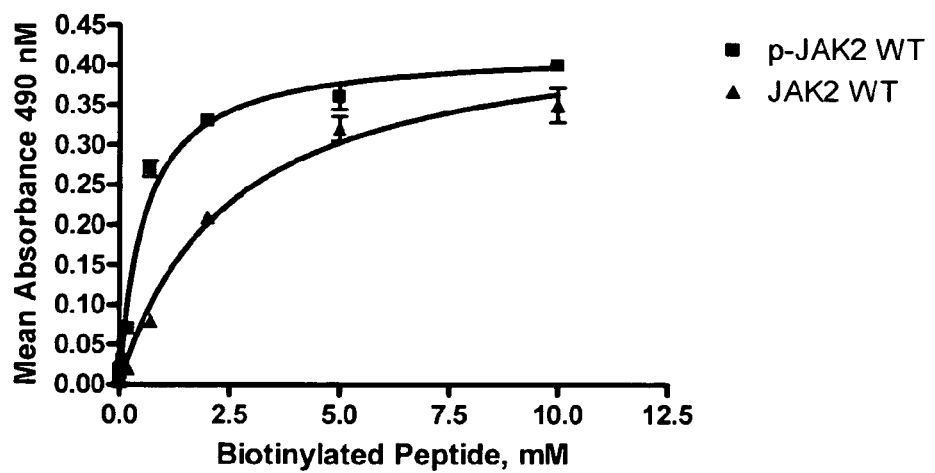
FIG. 4 shows binding of unphosphorylated JAK2 WT peptide versus phosphorylated JAK2 WT peptide to Tkip peptide. Various concentrations of biotinylated unphosphorylated JAK2 WT (JAK2 WT) and biotinylated phosphorylated JAK2 WT (p-JAK2 WT) peptides were incubated in the presence of immobilized Tkip. Binding was measured by solid phase binding assays. The data are representative of two independent experiments performed in triplicate. Binding of phosphorylated JAK2 WT peptide versus unphosphorylated JAK2 WT peptide was found to be statistically significant (p<0.005) by Student's t-test.

The binding data of FIG. 1 involved JAK2 WT peptide that was not phosphorylated at $^{1007}Y$. JAK2 WT recognition by SOCS-1 has been shown to involve phospho $^{1007}Y$ (Kile et al., 2002). Thus, Tkip does not need phosphorylation of $^{1007}Y$ in order to bind to JAK2 WT. However, the relative binding of Tkip to JAK2 WT unphosphorylated versus phosphorylation at $^{1007}Y$ (p-JAK2 WT) was determined. As shown in FIG. 4, Tkip bound both JAK2 WT and p-JAK2 WT in a dose-dependent manner, but binding was most efficient to p-JAK2 WT. Fifty percent endpoint concentrations were approximately 9-fold lower for p-JAK2 WT binding versus unphosphorylated JAK2 WT binding. Thus, phosphorylation of $^{1007}Y$ enhances Tkip binding to the JAK2 autophosphorylation site.

EXAMPLE 5

Tkip Peptide Inhibition of STAT1α Activation

Figure 5A:
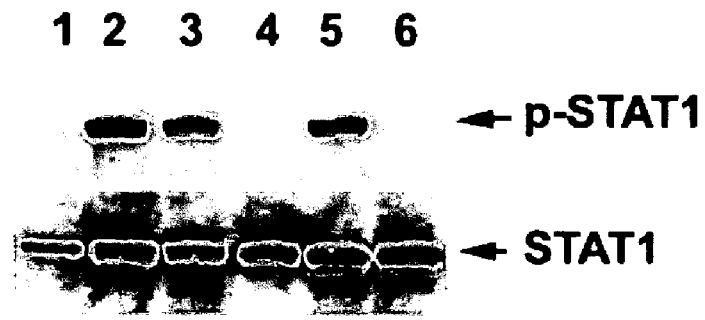
FIGS. 5A and 5B show that the Tkip peptide inhibits IFN-γ induced STAT1α activation in WISH cells but does not inhibit VEGF-induced activation of VEGFR in BAECs.
Figure 5B:
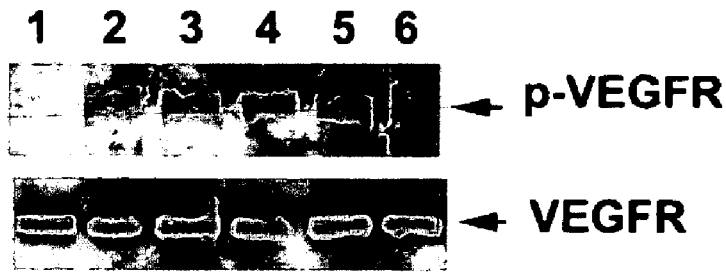

It has been firmly established that tyrosine phosphorylation of STAT1α at a specific tyrosine residue (Tyr 701) is required for the activation, dimerization, nuclear translocation, and subsequent downstream biological effects of IFN-γ stimulation (Kotenko et al., 2000). To assess whether Tkip could inhibit intracellular STAT1α activation, the effect of Tkip on STAT1α tyrosine phosphorylation in human fibroblast WISH cells was investigated. Cells were treated with Lipophilic Tkip and IFN-γ as indicated in FIG. 5A and whole cell lysates were examined using immunoblot analysis with antibodies specific for STAT1α and phosphorylated STAT1α. Cells pretreated with 8 μM Tkip for 17 hr and subsequently stimulated with 5000 U/ml IFN-γ for 30 min showed complete abolishment of IFN-γ induced STAT1α tyrosine phosphorylation. Cells pretreated with 1 μM Tkip and stimulated with IFN-γ showed no affect on STAT1α phosphorylation, suggesting that low concentrations of Tkip are not sufficient to inhibit IFN-γ induced phosphorylation of STAT1α. A lipophilic irrelevant peptide (MuIFN-γ(95–125), 8 μM) was used to show that the results observed were not dependent solely on the lipophilic modification of Tkip. Tyrosine phosphorylation of STAT1α was not affected in cells treated with IFN-γ in the absence of Tkip. As expected STAT1α phosphorylation was not observed in the absence of IFN-γ treatment. STAT1α protein levels in each treatment group were monitored by reprobing the membrane with anti-STAT1α antibodies. By contrast Tkip, under the same conditions, failed to inhibit VEGFR activation in bovine aortic endothelial cells as determined by autophosphorylation of VEGFR (FIG. 5B). These results clearly demonstrate the ability of Tkip to inhibit IFN-γ mediated intracellular phosphorylation of STAT1α at the level of the cell.

EXAMPLE 6

Tkip Peptide Inhibition of IFN-γ Induced Antiviral Activity

Figure 6:
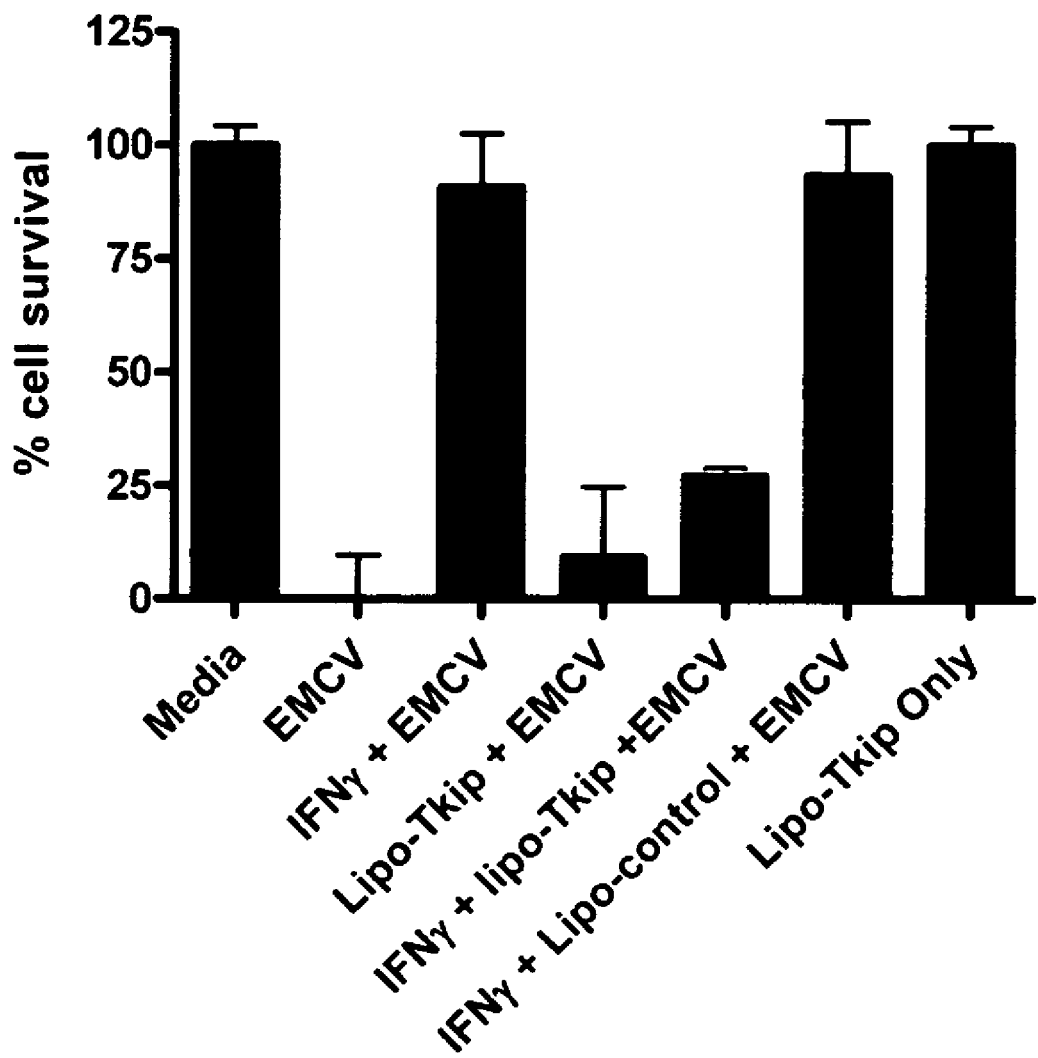
FIG. 6 shows that the Tkip peptide inhibits the antiviral activity of IFN-γ against EMC virus on WEHI-3 cells. WEHI-3 cells were preincubated either in the absence of peptide (Media), in the presence of IFN-γ (2000 U/ml) alone, or IFN-γ+10 μM of lipopeptides as indicated, for 24 hr. The control lipopeptide was the lipophilic version of JAK2 WT (see Table 3 for sequence). Cells were then challenged with EMC virus for another 24 hr. Cells were then stained with crystal violet, the dye extracted and the absorbance measured. Values are normalized percentages of cell survival determined by setting cells treated with EMC virus alone (EMCV) as 0% and cells with not virus treatment (Media) as 100%. The data are representative of at least two separate experiments. The difference in cell survival for cells incubated in the presence (IFN-γ+EMCV+Lipo-Tkip) or absence (IFN-γ+EMCV) of Lipo-Tkip was found to be statistically significant (p<0.005) by Student's t-test.
Figure 7A:
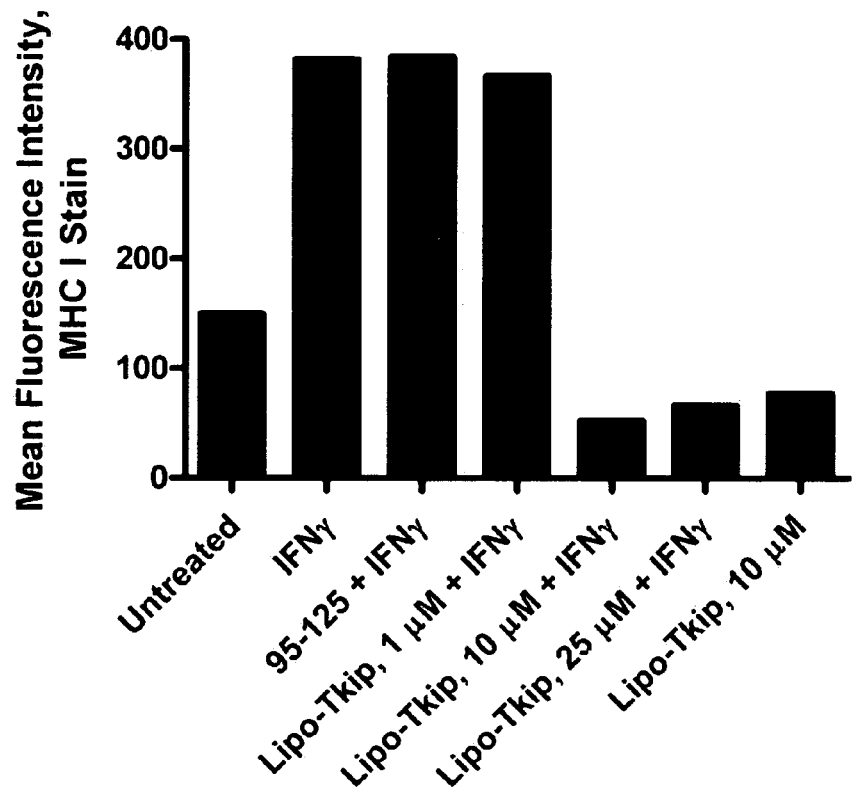
FIGS. 7A and 7B shows downregulation of IFN-γ induced cell membrane expression of MHC class I on WISH cells using Tkip peptide.
Figure 7B:
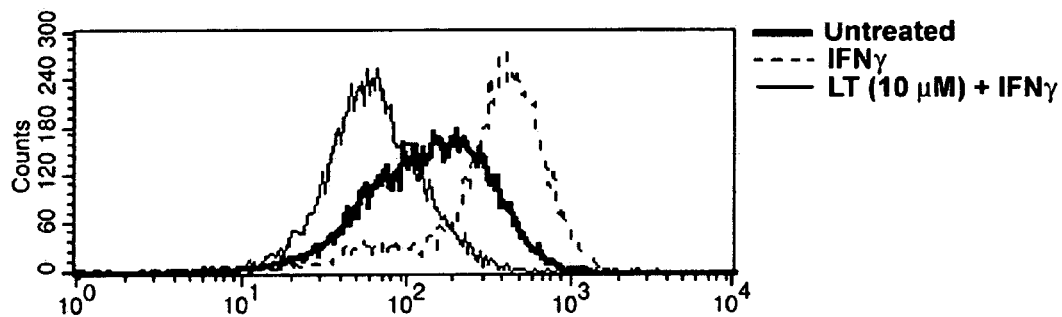
Figure 8:
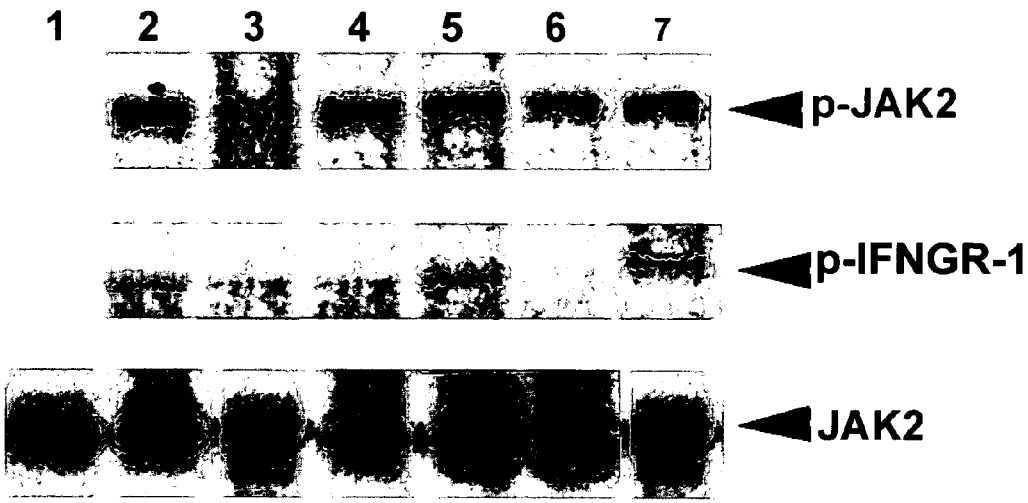
FIG. 8 shows inhibition of phosphorylation of kinases by peptides NGVLFLMIFHFLG (SEQ ID NO. 37) and EMLV-LLMALKLLA (SEQ ID NO. 72). Tkip inhibits autophosphorylation of JAK2. Tkip peptides, NGVLFLMIFHFLG (SEQ ID NO. 37), or EMLVLLMALKLLA (SEQ ID NO. 72) were added at 50 μM, where indicated, to in vitro kinase assays measuring JAK2 autophosphorylation. Kinase reactions were subjected to SDS-PAGE and the gels dried. Dried gels were subjected to autoradiography to detect $^{32}$P-labeled proteins (upper and middle panels). The negative control peptide was the JAK2 WT peptide used at the same concentration. Genistein, a nonspecific inhibitor of JAK2, was used as a positive control. Total JAK2 protein was measured from separate reactions that were subjected to SDS-PAGE and the proteins Western transferred to a nitrocellulose membrane followed by detection with standard immunoblotting and ECL detection protocols (bottom panel). The data are representative of at least two separate experiments.
Figure 9:
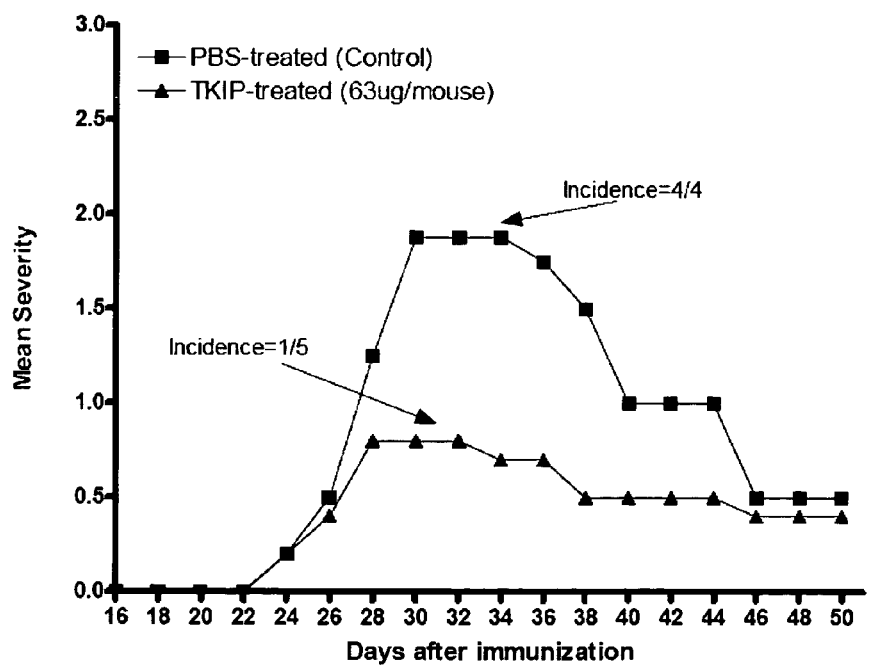
FIG. 9 shows Tkip suppresses experimental allergic encephalomyelitis (EAE) in mice. NZW mice were injected intraperitoneally with PBS or Tkip (63 μg/mouse) every other day starting the day of immunization with myelin basic protein (MBP) for induction of EAE. Mice were followed daily for signs of EAE, and mean severity of paralysis for each group was graded based on the following scale: 1, loss of tail tone, 2, hind leg weakness, 3, paraparesis, 4, paraplegia, 5, moribund, death. Control (PBS-treated) mice had an average severity of 2.1, while Tkip-treated mice had an average severity of 0.8. All mice in the control group had disease (disease incidence=4/4), while one mouse in the Tkip group had disease (disease incidence=1/5).

Functionally, since Tkip inhibits JAK2 autophosphorylation and subsequent phosphorylation of IFNGR-1, and phosphorylation of STAT1α, one would predict that Tkip would inhibit IFN-γ induced antiviral activity. WEHI-3 cells were infected with encephalomyocarditis (EMC) virus and the cells protected against EMC virus cytopathogenic effects (CPE) with 2000 U/ml mouse IFN-γ. Treatment of WEHI-3 cells with 10 μM Tkip (lipophilic for cell membrane penetration) along with IFN-γ resulted in approximately 75% reduction in IFN-γ antiviral activity as per increased CPE of EMC virus (FIG. 6). A lipophilic control peptide failed to affect IFN-γ antiviral activity, so the lipophilic Tkip effect was due to Tkip. Thus, consistent with inhibition of JAK2 tyrosine kinase activity, Tkip blocked the antiviral effects of IFN-γ.

EXAMPLE 7

Tkip Peptide Inhibition of Upregulation of MHC Class I Expression

Another well-established function of IFN-γ is the upregulation of MHC class I molecules on cells. Human WISH cells were treated with 5000 U/ml of human IFN-γ, which resulted in over 3-fold increase in MHC class I as per FACS analysis (FIG. 7). Lipophilic Tkip at 10 μM or 25 μM completely blocked upregulation of MHC class I expression, and in fact reduced the baseline constitutive expression of MHC class I molecules. A control lipophilic peptide (IFN-γ 95–125) had no effect. Thus, in addition to inhibition of IFN-γ antiviral activity, Tkip peptide also inhibited IFN-γ upregulation of MHC class I molecules. The fact that Tkip inhibited murine IFN-γ antiviral activity on WEHI cells (FIG. 6) and human IFN-γ upregulation of MHC class I molecules on human WISH cells (FIG. 7) is consistent with the autophosphorylation sites of murine and human JAK2 (Table 3) consisting of the same amino acid sequence.

EXAMPLE 8

Peptide Inhibition of Tyrosine Kinase Autophosphorylation

Experiments were also conducted to determine whether the peptide NGVLFLMIFHFLG (SEQ ID NO. 37) or the peptide EMLVLLMALKLLA (SEQ ID NO. 72) could inhibit JAK2 autophosphorylation as well as phosphorylation of IFN-γ receptor subunit IFNGR-1. As shown in FIG. 8, Tkip peptide at 50 μM inhibited both the autophosphorylation of JAK2 as well as JAK2 phosphorylation of IFNGR-1. A control peptide, JAK2 WT, at the same concentration had no effect on JAK2-induced tyrosine phosphorylations. The peptide NGVLFLMIFHFLG (SEQ ID NO. 37) did inhibit the JAK2-mediated phosphorylation of IFNGR-1 (lane 4 of FIG. 8, middle panel). The peptide EMLVLLMALKLLA (SEQ ID NO. 72) inhibited autophosphorylation of JAK2 (lane 7 of FIG. 4, upper panel), although it was not as effective as the Tkip peptide.

EXAMPLE 9

Protection of Mice from Experimental Allergic Encephalomyelitis by Tkip Peptide NZW mice were immunized with myelin basic protein (MBP) (300 ug) emulsified in complete Freund's adjuvant for the induction of experimental allergic encephalomyelitis (EAE). Tkip peptide (63 μg/mouse) was administered to mice every other day starting the day of immunization. Phosphate buffered saline (PBS) was used as the vehicle of transfer and as the control agent for the treatment of the control group. Mice were followed daily for signs of EAE and mean severity of paralysis for each group was graded based on the scale presented in the legend of FIG. 9. As shown in FIG. 9, all of the mice in the control group came down with EAE (incidence of disease=4/4), while only one out of 5 mice came down with EAE in the Tkip-treated group (incidence of disease=1/5). Furthermore, the mean severity of disease for the control group (2.1) was twice as high as that of the Tkip group (0.8) at its peak. The time of onset of disease for the control group and Tkip-treated group was similar (24 days post immnunization). Thus, treatment of MBP-immunized mice with Tkip peptide protects them from the autoimmune disease, EAE.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,912,183
U.S. Pat. No. 4,179,337
U.S. Pat. No. 5,763,585
U.S. Pat. No. 5,530,101
U.S. Pat. No. 5,585,089
U.S. Pat. No. 5,693,762
U.S. Pat. No. 6,180,370
U.S. Pat. No. 6,407,213
U.S. Pat. No. 5,106,739
U.S. Pat. No. 5,625,136
U.S. Pat. No. 5,034,322
Published U.S. patent application No. 20030032594
Published U.S. patent application No. 20020120100
Published U.S. patent application No. 20020035243
Alexander, W. S. (2002) "Suppressors of cytokine signalling (SOCS) in the immune system" *Nat. Rev. Immunol.* 2(6):410–416.
Alton, G., Schwambom, K., Satoh, Y., Westwick, J. K. (2002) "Therapeutic modulation of inflammatory gene transcription by kinase inhibitors" *Expert Opin Biol Ther.* 2:621–32.
Altschul, S. F. et al. (1990) "Basic Local Alignment Search Tool" *J. Mol. Biol.* 215:403–410.
Altschul, S. F. et al. (1997) "Gapped BLAST and PSI-BLAST: A New Generation of Protein Database Search Programs" *Nucl. Acids Res.* 25:3389–3402.
Andersson, L. C. (2002) "Significance of tyrosine kinases in cancer: overview" *Eur. J. Cancer* 38: Suppl. 5 S2.

Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266–285.

Blalock, J., E., K. L. Bost (1986) "Binding of peptides that are specified by complementary RNAs" *Biochem. J.* 234 (3):679–683.

Blume-Jensen, P., T. Hunter (2001) "Oncogenic kinase signalling" *Nature* 411(6835):355–365.

Capdeville, R., E. Buchdunger, J. Zimmermann, A. Matter (2002) "Glivec (STI571, imatinib), a rationally developed, targeted anticancer drug" *Nat. Rev. Drug Discov.* 1(7):493–502.

de Boer, H. A., Comstock, L. J., Vasser, M. (1983) "The tac promoter: a functional hybrid derived from the trp and lac promoters" *Proc. Natl. Acad. Sci. USA* 80(1):21–25.

Familletti, P. C., S. Rubinstein, S. Pestka (1981) "A convenient and rapid cytopathic effect inhibition assay for interferon" *Methods Enzymol.* 78(Pt A):387–394.

Fassina, G., G. Cassani, A. Corti (1992) "Binding of human tumor necrosis factor alpha to multimeric complementary peptides" *Arch. Biochem. Biophys.* 296(1):137–143.

Felgner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U.S.A.* 84(21):7413–7417.

Ferrara, N., H. P. Gerber, J. LeCouter (2003) "The biology of VEGF and its receptors" *Nat. Med.* 9(6):669–676.

Hanada, T., I. Kinjyo, K. Inagaki-Ohara, A. Yoshimura (2003) "Negative regulation of cytokine signaling by CIS/SOCS family proteins and their roles in inflammatory diseases" *Rev. Physiol. Biochem. Pharmacol.* 149:72–86.

Karlin S., Altschul, S. F. (1990) "Methods for Assessing the Statistical Significance of Molecular Sequence Features by Using General Scoring Schemes" *Proc. Natl. Acad. Sci. USA* 87:2264–2268.

Karlin S., Altschul, S. F. (1993) "Applications and Statistics for Multiple High-Scoring Segments in Molecular Sequences" *Proc. Natl. Acad. Sci. USA* 90:5873–5877.

Kile, B. T., B. A. Schulman, W. S. Alexander, N. A. Nicola, H. M. Martin, D. J. Hilton (2002) "The SOCS box: a tale of destruction and degradation" *Trends Biochem. Sci.* 27(5):235–241.

Kotenko, S. V., S. Pestka (2000) "Jak-Stat signal transduction pathway through the eyes of cytokine class II receptor complexes" *Oncogene* 19(21):2557–2565.

Kohler, G., C. Milstein (1975) "Continuous cultures of fused cells secreting antibody of predefined specificity" *Nature* 256(5517):495–497.

Larsen, L., C. Ropke (2002) "Suppressors of cytokine signalling: SOCS" *APMIS* 110(12):833–844.

Levitzki, A. (2002) "Tyrosine kinases as targets for cancer therapy" *Eur. J. Cancer* 38:Suppl. 5 S11–S18.

Maniatis, T., Fritsch, E. F., Sambrook, J. (1982) *Molecular Cloning: A Laboratory Manual*, Cold Spring Harbor Laboratory, Cold Spring Harbor, N.Y.

Merrifield, R. B. (1963) "Solid Phase Peptide Synthesis. I. The Synthesis of a Tetrapeptide" *J. Amer. Chem. Soc.* 85:2149–2154.

Ritter, C. A., C. L. Arteaga (2003) "The epidermal growth factor receptor-tyrosine kinase: a promising therapeutic target in solid tumors" *Semin. Oncol.* 30(1 Suppl 1):3–11.

Szente, B. E., Weiner, I. J., Jablonsky, M. J., Krishna, N. R., Torres, B. A., Johnson, H. M., Szente, B. E., Weiner, I. J., Jablonsky, M. J., Krishna, N. R., Torres, B. A., Johnson, H. M. (1996) "Structural requirements for agonist activity of a murine interferon-gamma peptide" *J Interferon Cytokine Res.* 16(10):813–817.

Tam, J. P. (1988) "Synthetic Peptide Vaccine Design: Synthesis and Properties of a High-Density Multiple Antigenic Peptide System" *Biochemistry* 85:5409–5413.

Tsygankov, A. Y. (2003) "Non-receptor protein tyrosine kinases" *Front. Biosci.* 8:S595–635.

Villain, M., P. L. Jackson, M. K. Manion, W. J. Dong, Z. Su, G. Fassina, T. M. Johnson, T. T. Sakai, N. R. Krishna, J. E. Blalock (2000) "De novo design of peptides targeted to the EF hands of calmodulin" *J. Biol. Chem.* 275(4): 2676–2685.

Wells, A. (1999) "EGF receptor" *Int. J. Biochem. Cell Biol.* 31(6):637–643.

Xia, L., L. Wang, A. S. Chung, S. S. Ivanov, M. Y. Ling, A. M. Dragoi, A. Platt, T. M. Gilmer, X. Y. Fu, Y. E. Chin (2002) "Identification of both positive and negative domains within the epidermal growth factor receptor COOH-terminal region for signal transducer and activator of transcription (STAT) activation" *J. Biol. Chem.* 277 (34):30716–30723.

Xu, D., McElroy, D., Thornburg, R. W., Wu, R. et al. (1993) "Systemic induction of a potato pin2 promoter by wounding, methyl jasmonate, and abscisic acid in transgenic rice plants" *Plant Molecular Biology* 22:573–588.

Yasukawa, H., H. Misawa, H. Sakamoto, M. Masuhara, A. Sasaki, T. Wakioka, S. Ohtsuka, T. Imaizumi, T. Matsuda, J. N. Ihle, A. Yoshimura (1999) "The JAK-binding protein JAB inhibits Janus tyrosine kinase activity through binding in the activation loop" *EMBO J.* 18(5):1309–1320.

Yu, Y, Hulmes, J. D., Herley, M. T., Whitney, R. G., Crabb, J. W., Sato, J. D. (2001) "Direct identification of a major autophosphorylation site on vascular endothelial growth factor receptor Flt-1 that mediates phosphatidylinositol 3'-kinase binding" *Biochem J.* 358(Pt 2):465–472.

We claim:

1. A peptide comprising the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase.

2. The peptide according to claim 1, wherein said protein kinase is a tyrosine kinase.

3. The peptide according to claim 2, wherein said tyrosine kinase is a JAK2 polypeptide.

4. The peptide according to claim 1, wherein said peptide consists of between about 5 to about 45 amino acids.

5. The peptide according to claim 1, wherein said peptide binds to an autophosphorylation site of said protein kinase and said autophosphorylation site has the amino acid sequence shown in SEQ ID NO. 2.

6. The peptide according to claim 1, wherein said peptide consists of the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36.

7. A composition comprising a peptide, wherein said peptide comprises the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, and wherein said peptide can bind to an autophosphorylation site of a protein kinase and thereby inhibit autophosphorylation of said protein kinase.

8. The composition according to claim 7, wherein said protein kinase is a tyrosine kinase.

9. The composition according to claim 8, wherein said tyrosine kinase is a JAK2 polypeptide.

10. The composition according to claim 7, wherein said peptide consists of between about 5 to about 45 amino acids.

11. The composition according to claim 7, wherein said composition comprises a pharmaceutically-acceptable carrier or diluent.

12. The composition according to claim 7, wherein said peptide binds to an autophosphorylation site of said protein kinase and said autophosphorylation site has the amino acid sequence shown in SEQ ID NO. 2.

13. The composition according to claim 7, wherein said peptide consists of the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36.

14. An isolated peptide that consists of the sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase.

15. The isolated peptide according to claim 14, wherein said protein kinase is a tyrosine kinase.

16. The isolated peptide according to claim 15, wherein said tyrosine kinase is a JAK2 polypeptide.

17. The isolated peptide according to claim 14, wherein said peptide binds to an autophosphorylation site of said protein kinase and said autophosphorylation site has the amino acid sequence shown in SEQ ID NO. 2.

18. A method for treating or preventing an autoimmune, inflammatory, cardiovascular, or oncological disorder in a human or animal, said method comprising administering to the human or animal an effective amount of:
   a) a peptide comprising the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase;
   b) a composition comprising a peptide, wherein said peptide comprises the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, and wherein said peptide can bind to an autophosphorylation site of a protein kinase and thereby inhibit autophosphorylation of said protein kinase; or
   c) an isolated peptide that consists of the sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase.

19. The method according to claim 18, wherein said inflammatory disorder is selected from the group consisting of arthritis, multiple sclerosis, lupus, Crohn's disease, diabetes, graft rejection, neurological disease, and an inflammatory connective tissue disease.

20. The method according to claim 18, wherein said oncological disorder is selected from the group consisting of cancer and/or tumors of the breast, kidney, mouth, larynx, esophagus, stomach, colon, ovary, lung, bladder, skin, muscle, pancreas, prostate, blood cells, and brain.

21. The method according to claim 18, wherein said oncological disorder is a leukemia.

22. A method for inhibiting autophosphorylation of a protein kinase, said method comprising contacting said protein kinase with:
   a) a peptide comprising the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of said protein kinase and thereby inhibit autophosphorylation of said protein kinase;
   b) a composition comprising a peptide, wherein said peptide comprises the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, and wherein said peptide can bind to an autophosphorylation site of said protein kinase and thereby inhibit autophosphorylation of said protein kinase; or
   c) an isolated peptide that consists of the sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of said protein kinase and thereby inhibit autophosphorylation of said protein kinase.

23. The method according to claim 22, wherein said protein kinase is a tyrosine kinase.

24. The method according to claim 23, wherein said tyrosine kinase is a JAK2 polypeptide.

25. The method according to claim 23, wherein said tyrosine kinase is an EGFR polypeptide.

26. The method according to claim 23, wherein said tyrosine kinase is erbB-1, erbB-2, erbB-3, or erbB-4.

27. The method according to claim 22, wherein said autophosphorylation site of said protein kinase comprises the amino acid sequence shown in SEQ ID NO. 2.

28. A kit comprising in one or more containers:
   a) a peptide comprising the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase;
   b) a composition comprising a peptide, wherein said peptide comprises the amino acid sequence shown in SEQ ID NO. 1, SEQ ID NO. 3, SEQ ID NO. 4, SEQ ID NO. 5, SEQ ID NO. 6 SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, and wherein said peptide can bind to an autophosphorylation site of a protein kinase and thereby inhibit autophosphorylation of said protein kinase; or
   c) an isolated peptide that consists of the sequence shown in SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase.

29. A method for inhibiting IFN-γ mediated activity of a cell, said method comprising contacting said cell with an effective amount of:
   a) a peptide comprising the amino acid sequence shown in SEQ ID NO. 1, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase;
   b) a composition comprising a peptide, wherein said peptide comprises the amino acid sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, and wherein said peptide can bind to an autophosphorylation site of a protein kinase and thereby inhibit autophosphorylation of said protein kinase; or
   c) an isolated peptide that consists of the sequence shown in SEQ ID NO. 1, SEQ ID NO. 3, SEQ ID NO. 4, SEQ ID NO. 5, SEQ ID NO. 6. SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24, SEQ ID NO. 25, SEQ ID NO. 26, SEQ ID NO. 27, SEQ ID NO. 28, SEQ ID NO. 29, SEQ ID NO. 30, SEQ ID NO. 31, SEQ ID NO. 32, SEQ ID NO. 33, SEQ ID NO. 34, SEQ ID NO. 35, or SEQ ID NO. 36, wherein said peptide can bind to an autophosphorylation site of a protein kinase and thereby inhibit autophosphorylation of said protein kinase.

30. The method according to claim 29, wherein said IFN-γ mediated activity is antiviral activity.

31. The method according to claim 30, wherein said IFN-γ mediated activity is upregulation of MHC class I molecules on cells.

32. The peptide according to claim 1, wherein said peptide comprises a chemical group that decreases an immunogenic response to said peptide or that extends the half-life of said peptide in vivo.

33. The peptide according to claim 32, wherein said chemical group is polyethylene glycol (PEG).

34. The peptide according to claim 1, wherein said peptide further comprises an amino acid sequence that allows said peptide to be translocated across a biological membrane.

35. The peptide according to claim 1, wherein said peptide consists of between about 5 to about 35 amino acids.

36. The composition according to claim 7, wherein said peptide comprises a chemical group that decreases an immunogenic response to said peptide or that extends the half-life of said peptide in vivo.

37. The composition according to claim 36, wherein said chemical group is polyethylene glycol (PEG).

38. The composition according to claim 7, wherein said peptide further comprises an amino acid sequence that allows said peptide to be translocated across a biological membrane.

39. The composition according to claim 7, wherein said peptide consists of between about 5 to about 35 amino acids.

40. The isolated peptide according to claim 14, wherein said peptide comprises a chemical group that decreases an immunogenic response to said peptide or that extends the half-life of said peptide in vivo.

41. The isolated peptide according to claim 40, wherein said chemical group is polyethylene glycol (PEG).

42. The method according to claim 18, wherein said peptide comprises a chemical group that decreases an immunogenic response to said peptide or that extends the half-life of said peptide in vivo.

43. The method according to claim 42, wherein said chemical group is polyethylene glycol (PEG).

44. The method according to claim 22, wherein said peptide comprises a chemical group that decreases an immunogenic response to said peptide or that extends the half-life of said peptide in vivo.

45. The method according to claim 44, wherein said chemical group is polyethylene glycol (PEG).

46. The kit according to claim 28, wherein said peptide comprises a chemical group that decreases an immunogenic response to said peptide or that extends the half-life of said peptide in vivo.

47. The kit according to claim 46, wherein said chemical group is polyethylene glycol (PEG).

48. The method according to claim 29, wherein said peptide comprises a chemical group that decreases an immunogenic response to said peptide or that extends the half-life of said peptide in vivo.

49. The method according to claim 48, wherein said chemical group is polyethylene glycol (PEG).

50. The method according to claim 18, wherein said disorder is an oncological disorder and said method further comprises administering one or more of an antitumor substance, radiation therapy, and surgical treatment.

\* \* \* \* \*

SEQUENCE LISTING

<160> NUMBER OF SEQ ID NOS: 76

<210> SEQ ID NO 1
<211> LENGTH: 12
<212> TYPE: PRT
<213> ORGANISM: Artificial sequence
<220> FEATURE:
<223> OTHER INFORMATION: amino acid sequence of a peptide that can be
      used according to the present invention

```
<400> SEQUENCE: 1

Trp Leu Val Phe Phe Val Ile Phe Tyr Phe Phe Arg
1               5                   10

<210> SEQ ID NO 2
<211> LENGTH: 13
<212> TYPE: PRT
<213> ORGANISM: Artificial sequence
<220> FEATURE:
<223> OTHER INFORMATION: amino acid sequence of a peptide used for
      control purposes

<400> SEQUENCE: 2

Leu Pro Gln Asp Lys Glu Tyr Tyr Lys Val Lys Glu Pro
1               5                   10

<210> SEQ ID NO 3
<211> LENGTH: 11
<212> TYPE: PRT
<213> ORGANISM: Artificial sequence
<220> FEATURE:
<223> OTHER INFORMATION: amino terminal deletion of the amino acid
      sequence shown in SEQ ID NO. 1

<400> SEQUENCE: 3

Leu Val Phe Phe Val Ile Phe Tyr Phe Phe Arg
1               5                   10

<210> SEQ ID NO 4
<211> LENGTH: 10
<212> TYPE: PRT
<213> ORGANISM: Artificial sequence
<220> FEATURE:
<223> OTHER INFORMATION: amino terminal deletion of the amino acid
      sequence shown in SEQ ID NO. 1

<400> SEQUENCE: 4

Val Phe Phe Val Ile Phe Tyr Phe Phe Arg
1               5                   10

<210> SEQ ID NO 5
<211> LENGTH: 9
<212> TYPE: PRT
<213> ORGANISM: Artificial sequence
<220> FEATURE:
<223> OTHER INFORMATION: amino terminal deletion of the amino acid
      sequence shown in SEQ ID NO. 1

<400> SEQUENCE: 5

Phe Phe Val Ile Phe Tyr Phe Phe Arg
1               5

<210> SEQ ID NO 6
<211> LENGTH: 8
<212> TYPE: PRT
<213> ORGANISM: Artificial sequence
<220> FEATURE:
<223> OTHER INFORMATION: amino terminal deletion of the amino acid
      sequence shown in SEQ ID NO. 1

<400> SEQUENCE: 6

Phe Val Ile Phe Tyr Phe Phe Arg
1               5

<210> SEQ ID NO 7
<211> LENGTH: 7
```

```
<212> TYPE: PRT
<213> ORGANISM: Artificial sequence
<220> FEATURE:
<223> OTHER INFORMATION: amino terminal deletion of the amino acid
      sequence shown in SEQ ID NO. 1

<400> SEQUENCE: 7

Val Ile Phe Tyr Phe Phe Arg
1               5

<210> SEQ ID NO 8
<211> LENGTH: 11
<212> TYPE: PRT
<213> ORGANISM: Artificial sequence
<220> FEATURE:
<223> OTHER INFORMATION: carboxy terminal deletion of the amino acid
      sequence shown in SEQ ID NO. 1

<400> SEQUENCE: 8

Trp Leu Val Phe Phe Val Ile Phe Tyr Phe Phe
1               5                   10

<210> SEQ ID NO 9
<211> LENGTH: 10
<212> TYPE: PRT
<213> ORGANISM: Artificial sequence
<220> FEATURE:
<223> OTHER INFORMATION: carboxy terminal deletion of the amino acid
      sequence shown in SEQ ID NO. 1

<400> SEQUENCE: 9

Trp Leu Val Phe Phe Val Ile Phe Tyr Phe
1               5                   10

<210> SEQ ID NO 10
<211> LENGTH: 9
<212> TYPE: PRT
<213> ORGANISM: Artificial sequence
<220> FEATURE:
<223> OTHER INFORMATION: carboxy terminal deletion of the amino acid
      sequence shown in SEQ ID NO. 1

<400> SEQUENCE: 10

Trp Leu Val Phe Phe Val Ile Phe Tyr
1               5

<210> SEQ ID NO 11
<211> LENGTH: 8
<212> TYPE: PRT
<213> ORGANISM: Artificial sequence
<220> FEATURE:
<223> OTHER INFORMATION: carboxy terminal deletion of the amino acid
      sequence shown in SEQ ID NO. 1

<400> SEQUENCE: 11

Trp Leu Val Phe Phe Val Ile Phe
1               5

<210> SEQ ID NO 12
<211> LENGTH: 7
<212> TYPE: PRT
<213> ORGANISM: Artificial sequence
<220> FEATURE:
<223> OTHER INFORMATION: carboxy terminal deletion of the amino acid
      sequence shown in SEQ ID NO. 1

<400> SEQUENCE: 12

Trp Leu Val Phe Phe Val Ile
```

```
1               5

<210> SEQ ID NO 13
<211> LENGTH: 10
<212> TYPE: PRT
<213> ORGANISM: Artificial sequence
<220> FEATURE:
<223> OTHER INFORMATION: amino and carboxy terminal deletion of the
      amino acid shown in SEQ ID NO. 1

<400> SEQUENCE: 13

Leu Val Phe Phe Val Ile Phe Tyr Phe Phe
1               5                   10

<210> SEQ ID NO 14
<211> LENGTH: 8
<212> TYPE: PRT
<213> ORGANISM: Artificial sequence
<220> FEATURE:
<223> OTHER INFORMATION: amino and carboxy terminal deletion of the
      amino acid sequence shown in SEQ ID NO. 1

<400> SEQUENCE: 14

Val Phe Phe Val Ile Phe Tyr Phe
1               5

<210> SEQ ID NO 15
<211> LENGTH: 6
<212> TYPE: PRT
<213> ORGANISM: Artificial sequence
<220> FEATURE:
<223> OTHER INFORMATION: amino and carboxy terminal deletion of the
      amino acid sequence shown in SEQ ID NO. 1

<400> SEQUENCE: 15

Phe Phe Val Ile Phe Tyr
1               5

<210> SEQ ID NO 16
<211> LENGTH: 13
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(1)
OTHER INFORMATION: any amino acid

<400> SEQUENCE: 16

Xaa Trp Leu Val Phe Phe Val Ile Phe Tyr Phe Phe Arg
1               5                   10

<210> SEQ ID NO 17
<211> LENGTH: 14
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(2)
<223> OTHER INFORMATION: any amino acid

<400> SEQUENCE: 17

Xaa Xaa Trp Leu Val Phe Phe Val Ile Phe Tyr Phe Phe Arg
1               5                   10
```

-continued

```
<210> SEQ ID NO 18
<211> LENGTH: 15
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(3)
<223> OTHER INFORMATION: any amino acid

<400> SEQUENCE: 18

Xaa Xaa Xaa Trp Leu Val Phe Phe Val Ile Phe Tyr Phe Phe Arg
 1               5                  10                  15

<210> SEQ ID NO 19
<211> LENGTH: 16
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(4)
<223> OTHER INFORMATION: any amino acid

<400> SEQUENCE: 19

Xaa Xaa Xaa Xaa Trp Leu Val Phe Phe Val Ile Phe Tyr Phe Phe Arg
 1               5                  10                  15

<210> SEQ ID NO 20
<211> LENGTH: 17
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(5)
<223> OTHER INFORMATION: any amino acid

<400> SEQUENCE: 20

Xaa Xaa Xaa Xaa Xaa Trp Leu Val Phe Phe Val Ile Phe Tyr Phe Phe
 1               5                  10                  15

Arg

<210> SEQ ID NO 21
<211> LENGTH: 22
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(10)
<223> OTHER INFORMATION: any amino acid

<400> SEQUENCE: 21

Xaa Xaa Xaa Xaa Xaa Xaa Xaa Xaa Xaa Xaa Trp Leu Val Phe Phe Val
 1               5                  10                  15

Ile Phe Tyr Phe Phe Arg
                20
```

```
<210> SEQ ID NO 22
<211> LENGTH: 27
<212> TYPE: PRT
<213> ORGANISM: Artificial sequence
<220> FEATURE:
<223> OTHER INFORMATION: amino terminal addition of the amino acid
      sequence shown in SEQ ID NO. 1
<220> FEATURE:
<221> NAME/KEY: MISC_FEATURE
<222> LOCATION: (1)..(15)
<223> OTHER INFORMATION: any amino acid

<400> SEQUENCE: 22

Xaa Xaa Xaa Xaa Xaa Xaa Xaa Xaa Xaa Xaa Xaa Xaa Xaa Xaa Xaa Trp
1               5                   10                  15

Leu Val Phe Phe Val Ile Phe Tyr Phe Phe Arg
            20                  25

<210> SEQ ID NO 23
<211> LENGTH: 13
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(13)
<223> OTHER INFORMATION: any amino acid

<400> SEQUENCE: 23

Trp Leu Val Phe Phe Val Ile Phe Tyr Phe Phe Arg Xaa
1               5                   10

<210> SEQ ID NO 24
<211> LENGTH: 14
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(14)
<223> OTHER INFORMATION: any amino acid

<400> SEQUENCE: 24

Trp Leu Val Phe Phe Val Ile Phe Tyr Phe Phe Arg Xaa Xaa
1               5                   10

<210> SEQ ID NO 25
<211> LENGTH: 15
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(15)
<223> OTHER INFORMATION: any amino acid

<400> SEQUENCE: 25

Trp Leu Val Phe Phe Val Ile Phe Tyr Phe Phe Arg Xaa Xaa Xaa
1               5                   10                  15

<210> SEQ ID NO 26
<211> LENGTH: 16
<212> TYPE: PRT
<213> ORGANISM: Artificial sequence
```

```
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(16)
<223> OTHER INFORMATION: any amino acid

<400> SEQUENCE: 26

Trp Leu Val Phe Phe Val Ile Phe Tyr Phe Phe Arg Xaa Xaa Xaa Xaa
1               5                   10                  15

<210> SEQ ID NO 27
<211> LENGTH: 17
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(17)
<223> OTHER INFORMATION: any amino acid

<400> SEQUENCE: 27

Trp Leu Val Phe Phe Val Ile Phe Tyr Phe Phe Arg Xaa Xaa Xaa Xaa
1               5                   10                  15

Xaa

<210> SEQ ID NO 28
<211> LENGTH: 22
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(22)
<223> OTHER INFORMATION: any amino acid

<400> SEQUENCE: 28

Trp Leu Val Phe Phe Val Ile Phe Tyr Phe Phe Arg Xaa Xaa Xaa Xaa
1               5                   10                  15

Xaa Xaa Xaa Xaa Xaa Xaa
            20

<210> SEQ ID NO 29
<211> LENGTH: 27
<212> TYPE: PRT
<213> ORGANISM: Artificial sequence
<220> FEATURE:
<223> OTHER INFORMATION: carboxy terminal addition of the amino acid
      sequence shown in SEQ ID NO. 1
<220> FEATURE:
<221> NAME/KEY: MISC_FEATURE
<222> LOCATION: (13)..(27)
<223> OTHER INFORMATION: any amino acid

<400> SEQUENCE: 29

Trp Leu Val Phe Phe Val Ile Phe Tyr Phe Phe Arg Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 30
<211> LENGTH: 14
<212> TYPE: PRT
```

```
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (14)..(14)
<223> OTHER INFORMATION: any amino acid

<400> SEQUENCE: 30

Xaa Trp Leu Val Phe Phe Val Ile Phe Tyr Phe Phe Arg Xaa
1               5                   10

<210> SEQ ID NO 31
<211> LENGTH: 16
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(2)
<223> OTHER INFORMATION: any amino acid
<220> FEATURE:
<221> NAME/KEY: MISC_FEATURE
<222> LOCATION: (15)..(16)
<223> OTHER INFORMATION: any amino acid

<400> SEQUENCE: 31

Xaa Xaa Trp Leu Val Phe Phe Val Ile Phe Tyr Phe Phe Arg Xaa Xaa
1               5                   10                  15

<210> SEQ ID NO 32
<211> LENGTH: 18
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(3)
<223> OTHER INFORMATION: any amino acid
<220> FEATURE:
<221> NAME/KEY: MISC_FEATURE
<222> LOCATION: (16)..(18)
<223> OTHER INFORMATION: any amino acid

<400> SEQUENCE: 32

Xaa Xaa Xaa Trp Leu Val Phe Phe Val Ile Phe Tyr Phe Phe Arg Xaa
1               5                   10                  15

Xaa Xaa

<210> SEQ ID NO 33
<211> LENGTH: 20
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(4)
<223> OTHER INFORMATION: any amino acid
<220> FEATURE:
<221> NAME/KEY: MISC_FEATURE
<222> LOCATION: (17)..(20)
```

<223> OTHER INFORMATION: any amino acid

<400> SEQUENCE: 33

Xaa Xaa Xaa Xaa Trp Leu Val Phe Phe Val Ile Phe Tyr Phe Phe Arg
1               5                   10                  15

Xaa Xaa Xaa Xaa
            20

<210> SEQ ID NO 34
<211> LENGTH: 22
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(5)
<223> OTHER INFORMATION: any amino acid
<220> FEATURE:
<221> NAME/KEY: MISC_FEATURE
<222> LOCATION: (18)..(22)
<223> OTHER INFORMATION: any amino acid

<400> SEQUENCE: 34

Xaa Xaa Xaa Xaa Xaa Trp Leu Val Phe Phe Val Ile Phe Tyr Phe Phe
1               5                   10                  15

Arg Xaa Xaa Xaa Xaa Xaa
            20

<210> SEQ ID NO 35
<211> LENGTH: 32
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(10)
<223> OTHER INFORMATION: any amino acid
<220> FEATURE:
<221> NAME/KEY: MISC_FEATURE
<222> LOCATION: (23)..(32)
<223> OTHER INFORMATION: any amino acid

<400> SEQUENCE: 35

Xaa Xaa Xaa Xaa Xaa Xaa Xaa Xaa Xaa Xaa Trp Leu Val Phe Phe Val
1               5                   10                  15

Ile Phe Tyr Phe Phe Arg Xaa Xaa Xaa Xaa Xaa Xaa Xaa Xaa Xaa Xaa
            20                  25                  30

<210> SEQ ID NO 36
<211> LENGTH: 42
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 1
<220> FEATURE:
<221> NAME/KEY: MISC_FEATURE
<222> LOCATION: (1)..(15)
<223> OTHER INFORMATION: any amino acid
<220> FEATURE:
<221> NAME/KEY: MISC_FEATURE
<222> LOCATION: (28)..(42)
<223> OTHER INFORMATION: any amino acid

<400> SEQUENCE: 36

```
Xaa Xaa Xaa Xaa Xaa Xaa Xaa Xaa Xaa Xaa Xaa Xaa Xaa Xaa Trp
1               5                   10                  15

Leu Val Phe Phe Val Ile Phe Tyr Phe Phe Arg Xaa Xaa Xaa Xaa
            20                  25                  30

Xaa Xaa Xaa Xaa Xaa Xaa Xaa Xaa Xaa Xaa
        35                  40
```

<210> SEQ ID NO 37
<211> LENGTH: 13
<212> TYPE: PRT
<213> ORGANISM: Artificial sequence
<220> FEATURE:
<223> OTHER INFORMATION: amino acid sequence of a peptide that can be
      used according to the present invention

<400> SEQUENCE: 37

```
Asn Gly Val Leu Phe Leu Met Ile Phe His Phe Leu Gly
1               5                   10
```

<210> SEQ ID NO 38
<211> LENGTH: 12
<212> TYPE: PRT
<213> ORGANISM: Artificial sequence
<220> FEATURE:
<223> OTHER INFORMATION: amino terminal deletion of the amino acid
      sequence shown in SEQ ID NO. 37

<400> SEQUENCE: 38

```
Gly Val Leu Phe Leu Met Ile Phe His Phe Leu Gly
1               5                   10
```

<210> SEQ ID NO 39
<211> LENGTH: 11
<212> TYPE: PRT
<213> ORGANISM: Artificial sequence
<220> FEATURE:
<223> OTHER INFORMATION: amino terminal deletion of the amino acid
      sequence shown in SEQ ID NO. 37

<400> SEQUENCE: 39

```
Val Leu Phe Leu Met Ile Phe His Phe Leu Gly
1               5                   10
```

<210> SEQ ID NO 40
<211> LENGTH: 10
<212> TYPE: PRT
<213> ORGANISM: Artificial sequence
<220> FEATURE:
<223> OTHER INFORMATION: amino terminal deletion of the amino acid
      sequence shown in SEQ ID NO. 37

<400> SEQUENCE: 40

```
Leu Phe Leu Met Ile Phe His Phe Leu Gly
1               5                   10
```

<210> SEQ ID NO 41
<211> LENGTH: 9
<212> TYPE: PRT
<213> ORGANISM: Artificial sequence
<220> FEATURE:
<223> OTHER INFORMATION: amino terminal deletion of the amino acid
      sequence shown in SEQ ID NO. 37

<400> SEQUENCE: 41

```
Phe Leu Met Ile Phe His Phe Leu Gly
1               5
```

```
<210> SEQ ID NO 42
<211> LENGTH: 8
<212> TYPE: PRT
<213> ORGANISM: Artificial sequence
<220> FEATURE:
<223> OTHER INFORMATION: amino terminal deletion of the amino acid
      sequence shown in SEQ ID NO. 37

<400> SEQUENCE: 42

Leu Met Ile Phe His Phe Leu Gly
1               5

<210> SEQ ID NO 43
<211> LENGTH: 12
<212> TYPE: PRT
<213> ORGANISM: Artificial sequence
<220> FEATURE:
<223> OTHER INFORMATION: carboxy terminal deletion of the amino acid
      sequence shown in SEQ ID NO. 37

<400> SEQUENCE: 43

Asn Gly Val Leu Phe Leu Met Ile Phe His Phe Leu
1               5                   10

<210> SEQ ID NO 44
<211> LENGTH: 11
<212> TYPE: PRT
<213> ORGANISM: Artificial sequence
<220> FEATURE:
<223> OTHER INFORMATION: carboxy terminal deletion of the amino acid
      sequence shown in SEQ ID NO. 37

<400> SEQUENCE: 44

Asn Gly Val Leu Phe Leu Met Ile Phe His Phe
1               5                   10

<210> SEQ ID NO 45
<211> LENGTH: 10
<212> TYPE: PRT
<213> ORGANISM: Artificial sequence
<220> FEATURE:
<223> OTHER INFORMATION: carboxy terminal deletion of the amino acid
      sequence shown in SEQ ID NO. 37

<400> SEQUENCE: 45

Asn Gly Val Leu Phe Leu Met Ile Phe His
1               5                   10

<210> SEQ ID NO 46
<211> LENGTH: 9
<212> TYPE: PRT
<213> ORGANISM: Artificial sequence
<220> FEATURE:
<223> OTHER INFORMATION: carboxy terminal deletion of the amino acid
      sequence shown in SEQ ID NO. 37

<400> SEQUENCE: 46

Asn Gly Val Leu Phe Leu Met Ile Phe
1               5

<210> SEQ ID NO 47
<211> LENGTH: 8
<212> TYPE: PRT
<213> ORGANISM: Artificial sequence
<220> FEATURE:
<223> OTHER INFORMATION: carboxy terminal deletion of the amino acid
      sequence shown in SEQ ID NO. 37
```

```
<400> SEQUENCE: 47

Asn Gly Val Leu Phe Leu Met Ile
1               5

<210> SEQ ID NO 48
<211> LENGTH: 11
<212> TYPE: PRT
<213> ORGANISM: Artificial sequence
<220> FEATURE:
<223> OTHER INFORMATION: amino and carboxy terminal deletion of the
      amino acid shown in SEQ ID NO. 37

<400> SEQUENCE: 48

Gly Val Leu Phe Leu Met Ile Phe His Phe Leu
1               5                   10

<210> SEQ ID NO 49
<211> LENGTH: 9
<212> TYPE: PRT
<213> ORGANISM: Artificial sequence
<220> FEATURE:
<223> OTHER INFORMATION: amino and carboxy terminal deletion of the
      amino acid shown in SEQ ID NO. 37

<400> SEQUENCE: 49

Val Leu Phe Leu Met Ile Phe His Phe
1               5

<210> SEQ ID NO 50
<211> LENGTH: 7
<212> TYPE: PRT
<213> ORGANISM: Artificial sequence
<220> FEATURE:
<223> OTHER INFORMATION: amino and carboxy terminal deletion of the
      amino acid shown in SEQ ID NO. 37

<400> SEQUENCE: 50

Leu Phe Leu Met Ile Phe His
1               5

<210> SEQ ID NO 51
<211> LENGTH: 14
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(1)
<223> OTHER INFORMATION: any amino acid

<400> SEQUENCE: 51

Xaa Asn Gly Val Leu Phe Leu Met Ile Phe His Phe Leu Gly
1               5                   10

<210> SEQ ID NO 52
<211> LENGTH: 15
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(2)
<223> OTHER INFORMATION: any amino acid

<400> SEQUENCE: 52
```

```
Xaa Xaa Asn Gly Val Leu Phe Leu Met Ile Phe His Phe Leu Gly
1               5                   10                  15
```

<210> SEQ ID NO 53
<211> LENGTH: 16
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(3)
<223> OTHER INFORMATION: any amino acid

<400> SEQUENCE: 53

```
Xaa Xaa Xaa Asn Gly Val Leu Phe Leu Met Ile Phe His Phe Leu Gly
1               5                   10                  15
```

<210> SEQ ID NO 54
<211> LENGTH: 17
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(4)
<223> OTHER INFORMATION: any amino acid

<400> SEQUENCE: 54

```
Xaa Xaa Xaa Xaa Asn Gly Val Leu Phe Leu Met Ile Phe His Phe Leu
1               5                   10                  15

Gly
```

<210> SEQ ID NO 55
<211> LENGTH: 18
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(5)
<223> OTHER INFORMATION: any amino acid

<400> SEQUENCE: 55

```
Xaa Xaa Xaa Xaa Xaa Asn Gly Val Leu Phe Leu Met Ile Phe His Phe
1               5                   10                  15

Leu Gly
```

<210> SEQ ID NO 56
<211> LENGTH: 23
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(10)
<223> OTHER INFORMATION: any amino acid

<400> SEQUENCE: 56

```
Xaa Xaa Xaa Xaa Xaa Xaa Xaa Xaa Xaa Xaa Asn Gly Val Leu Phe Leu
1               5                   10                  15
```

```
Met Ile Phe His Phe Leu Gly
                20
```

<210> SEQ ID NO 57
<211> LENGTH: 28
<212> TYPE: PRT
<213> ORGANISM: Artificial sequence
<220> FEATURE:
<223> OTHER INFORMATION: amino terminal addition of the amino acid
      sequence shown in SEQ ID NO. 37
<220> FEATURE:
<221> NAME/KEY: MISC_FEATURE
<222> LOCATION: (1)..(15)
<223> OTHER INFORMATION: any amino acid

<400> SEQUENCE: 57

```
Xaa Xaa Xaa Xaa Xaa Xaa Xaa Xaa Xaa Xaa Xaa Xaa Xaa Xaa Xaa Asn
1               5                   10                  15

Gly Val Leu Phe Leu Met Ile Phe His Phe Leu Gly
                20                  25
```

<210> SEQ ID NO 58
<211> LENGTH: 14
<212> TYPE: PRT
<213> ORGANISM: Artificial sequence
<220> FEATURE:
<223> OTHER INFORMATION: carboxy terminal addition of the amino acid
      sequence shown in SEQ ID NO. 37
<220> FEATURE:
<221> NAME/KEY: MISC_FEATURE
<222> LOCATION: (14)..(14)
<223> OTHER INFORMATION: any amino acid

<400> SEQUENCE: 58

```
Asn Gly Val Leu Phe Leu Met Ile Phe His Phe Leu Gly Xaa
1               5                   10
```

<210> SEQ ID NO 59
<211> LENGTH: 15
<212> TYPE: PRT
<213> ORGANISM: Artificial sequence
<220> FEATURE:
<223> OTHER INFORMATION: carboxy terminal addition of the amino acid
      sequence shown in SEQ ID NO. 37
<220> FEATURE:
<221> NAME/KEY: MISC_FEATURE
<222> LOCATION: (14)..(15)
<223> OTHER INFORMATION: any amino acid

<400> SEQUENCE: 59

```
Asn Gly Val Leu Phe Leu Met Ile Phe His Phe Leu Gly Xaa Xaa
1               5                   10                  15
```

<210> SEQ ID NO 60
<211> LENGTH: 16
<212> TYPE: PRT
<213> ORGANISM: Artificial sequence
<220> FEATURE:
<223> OTHER INFORMATION: carboxy terminal addition of the amino acid
      sequence shown in SEQ ID NO. 37
<220> FEATURE:
<221> NAME/KEY: MISC_FEATURE
<222> LOCATION: (14)..(16)
<223> OTHER INFORMATION: any amino acid

<400> SEQUENCE: 60

```
Asn Gly Val Leu Phe Leu Met Ile Phe His Phe Leu Gly Xaa Xaa Xaa
1               5                   10                  15
```

<210> SEQ ID NO 61
<211> LENGTH: 17
<212> TYPE: PRT
<213> ORGANISM: Artificial sequence
<220> FEATURE:
<223> OTHER INFORMATION: carboxy terminal addition of the amino acid
     sequence shown in SEQ ID NO. 37
<220> FEATURE:
<221> NAME/KEY: MISC_FEATURE
<222> LOCATION: (14)..(17)
<223> OTHER INFORMATION: any amino acid

<400> SEQUENCE: 61

Asn Gly Val Leu Phe Leu Met Ile Phe His Phe Leu Gly Xaa Xaa Xaa
1               5                   10                  15

Xaa

<210> SEQ ID NO 62
<211> LENGTH: 18
<212> TYPE: PRT
<213> ORGANISM: Artificial sequence
<220> FEATURE:
<223> OTHER INFORMATION: carboxy terminal addition of the amino acid
     sequence shown in SEQ ID NO. 37
<220> FEATURE:
<221> NAME/KEY: MISC_FEATURE
<222> LOCATION: (14)..(18)
<223> OTHER INFORMATION: any amino acid

<400> SEQUENCE: 62

Asn Gly Val Leu Phe Leu Met Ile Phe His Phe Leu Gly Xaa Xaa Xaa
1               5                   10                  15

Xaa Xaa

<210> SEQ ID NO 63
<211> LENGTH: 23
<212> TYPE: PRT
<213> ORGANISM: Artificial sequence
<220> FEATURE:
<223> OTHER INFORMATION: carboxy terminal addition of the amino acid
     sequence shown in SEQ ID NO. 37
<220> FEATURE:
<221> NAME/KEY: MISC_FEATURE
<222> LOCATION: (14)..(23)
<223> OTHER INFORMATION: any amino acid

<400> SEQUENCE: 63

Asn Gly Val Leu Phe Leu Met Ile Phe His Phe Leu Gly Xaa Xaa Xaa
1               5                   10                  15

Xaa Xaa Xaa Xaa Xaa Xaa Xaa
            20

<210> SEQ ID NO 64
<211> LENGTH: 28
<212> TYPE: PRT
<213> ORGANISM: Artificial sequence
<220> FEATURE:
<223> OTHER INFORMATION: carboxy terminal addition of the amino acid
     sequence shown in SEQ ID NO. 37
<220> FEATURE:
<221> NAME/KEY: MISC_FEATURE
<222> LOCATION: (14)..(28)
<223> OTHER INFORMATION: any amino acid

<400> SEQUENCE: 64

Asn Gly Val Leu Phe Leu Met Ile Phe His Phe Leu Gly Xaa Xaa Xaa
1               5                   10                  15

```
Xaa Xaa Xaa Xaa Xaa Xaa Xaa Xaa Xaa Xaa Xaa Xaa
            20                  25
```

<210> SEQ ID NO 65
<211> LENGTH: 15
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (15)..(15)
<223> OTHER INFORMATION: any amino acid

<400> SEQUENCE: 65

```
Xaa Asn Gly Val Leu Phe Leu Met Ile Phe His Phe Leu Gly Xaa
1               5                   10                  15
```

<210> SEQ ID NO 66
<211> LENGTH: 17
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(2)
<223> OTHER INFORMATION: any amino acid
<220> FEATURE:
<221> NAME/KEY: MISC_FEATURE
<222> LOCATION: (16)..(17)
<223> OTHER INFORMATION: any amino acid

<400> SEQUENCE: 66

```
Xaa Xaa Asn Gly Val Leu Phe Leu Met Ile Phe His Phe Leu Gly Xaa
1               5                   10                  15

Xaa
```

<210> SEQ ID NO 67
<211> LENGTH: 19
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(3)
<223> OTHER INFORMATION: any amino acid
<220> FEATURE:
<221> NAME/KEY: MISC_FEATURE
<222> LOCATION: (17)..(19)
<223> OTHER INFORMATION: any amino acid

<400> SEQUENCE: 67

```
Xaa Xaa Xaa Asn Gly Val Leu Phe Leu Met Ile Phe His Phe Leu Gly
1               5                   10                  15

Xaa Xaa Xaa
```

<210> SEQ ID NO 68
<211> LENGTH: 21
<212> TYPE: PRT
<213> ORGANISM: Artificial sequence
<220> FEATURE:

```
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(4)
<223> OTHER INFORMATION: any amino acid
<220> FEATURE:
<221> NAME/KEY: MISC_FEATURE
<222> LOCATION: (18)..(21)
<223> OTHER INFORMATION: any amino acid

<400> SEQUENCE: 68

Xaa Xaa Xaa Xaa Asn Gly Val Leu Phe Leu Met Ile Phe His Phe Leu
1               5                   10                  15

Gly Xaa Xaa Xaa Xaa
            20

<210> SEQ ID NO 69
<211> LENGTH: 23
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(5)
<223> OTHER INFORMATION: any amino acid
<220> FEATURE:
<221> NAME/KEY: MISC_FEATURE
<222> LOCATION: (19)..(23)
<223> OTHER INFORMATION: any amino acid

<400> SEQUENCE: 69

Xaa Xaa Xaa Xaa Xaa Asn Gly Val Leu Phe Leu Met Ile Phe His Phe
1               5                   10                  15

Leu Gly Xaa Xaa Xaa Xaa Xaa
            20

<210> SEQ ID NO 70
<211> LENGTH: 33
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
<220> FEATURE:
<221> NAME/KEY: MISC_FEATURE
<222> LOCATION: (1)..(10)
<223> OTHER INFORMATION: any amino acid
<220> FEATURE:
<221> NAME/KEY: MISC_FEATURE
<222> LOCATION: (24)..(33)
<223> OTHER INFORMATION: any amino acid

<400> SEQUENCE: 70

Xaa Xaa Xaa Xaa Xaa Xaa Xaa Xaa Xaa Xaa Asn Gly Val Leu Phe Leu
1               5                   10                  15

Met Ile Phe His Phe Leu Gly Xaa Xaa Xaa Xaa Xaa Xaa Xaa Xaa
            20                  25                  30

Xaa

<210> SEQ ID NO 71
<211> LENGTH: 43
<212> TYPE: PRT
<213> ORGANISM: Artificial sequence
<220> FEATURE:
<223> OTHER INFORMATION: amino and carboxy terminal addition of the
      amino acid sequence shown in SEQ ID NO. 37
```

```
<220> FEATURE:
<221> NAME/KEY: MISC_FEATURE
<222> LOCATION: (1)..(15)
<223> OTHER INFORMATION: any amino acid
<220> FEATURE:
<221> NAME/KEY: MISC_FEATURE
<222> LOCATION: (29)..(43)
<223> OTHER INFORMATION: any amino acid

<400> SEQUENCE: 71

Xaa Xaa Xaa Xaa Xaa Xaa Xaa Xaa Xaa Xaa Xaa Xaa Xaa Xaa Xaa Asn
1               5                   10                  15

Gly Val Leu Phe Leu Met Ile Phe His Phe Leu Gly Xaa Xaa Xaa Xaa
            20                  25                  30

Xaa Xaa Xaa Xaa Xaa Xaa Xaa Xaa Xaa Xaa Xaa
        35                  40

<210> SEQ ID NO 72
<211> LENGTH: 13
<212> TYPE: PRT
<213> ORGANISM: Artificial sequence
<220> FEATURE:
<223> OTHER INFORMATION: amino acid sequence of a peptide that can be
      used according to the present invention

<400> SEQUENCE: 72

Glu Met Leu Val Leu Leu Met Ala Leu Lys Leu Leu Ala
1               5                   10

<210> SEQ ID NO 73
<211> LENGTH: 15
<212> TYPE: PRT
<213> ORGANISM: Artificial sequence
<220> FEATURE:
<223> OTHER INFORMATION: amino acid sequence of a peptide used for
      control purposes

<400> SEQUENCE: 73

Lys Val Glu Lys Ile Gly Glu Gly Thr Tyr Gly Val Val Tyr Lys
1               5                   10                  15

<210> SEQ ID NO 74
<211> LENGTH: 13
<212> TYPE: PRT
<213> ORGANISM: Artificial sequence
<220> FEATURE:
<223> OTHER INFORMATION: amino acid sequence of a peptide used for
      control purposes

<400> SEQUENCE: 74

Ser Ser Asp Val Arg Tyr Val Asn Ala Phe Lys Phe Met
1               5                   10

<210> SEQ ID NO 75
<211> LENGTH: 21
<212> TYPE: PRT
<213> ORGANISM: Artificial sequence
<220> FEATURE:
<223> OTHER INFORMATION: amino acid sequence of a peptide used for
      control purposes

<400> SEQUENCE: 75

Lys Thr Glu Gly Val Pro Ser Thr Ala Ile Arg Glu Ile Ser Leu Leu
1               5                   10                  15

Lys Glu Leu Asn His
            20
```

```
<210> SEQ ID NO 76
<211> LENGTH: 31
<212> TYPE: PRT
<213> ORGANISM: Artificial sequence
<220> FEATURE:
<223> OTHER INFORMATION: amino acid sequence of a peptide used for
      control purposes

<400> SEQUENCE: 76

Ala Lys Phe Glu Val Asn Asn Pro Gln Val Gln Arg Gln Ala Phe Asn
1               5                   10                  15

Glu Leu Ile Arg Val Val His Gln Leu Leu Pro Glu Ser Ser Leu
            20                  25                  30
```